United States Patent [19]
Applegate

[11] Patent Number: 5,360,010
[45] Date of Patent: * Nov. 1, 1994

[54] VASCULAR ENTOPTOSCOPE

[75] Inventor: Raymond A. Applegate, San Antonio, Tex., Arthur Bradley, Bloomington, IN.

[73] Assignee: Board of Regents, The University of Texas System, Austin, Tex.

[ * ] Notice: The portion of the term of this patent subsequent to May 21, 2008 has been disclaimed.

[21] Appl. No.: 946,321

[22] PCT Filed: Jan. 5, 1991

[86] PCT No.: PCT/US91/02996

§ 371 Date: Nov. 2, 1992

§ 102(e) Date: Nov. 2, 1992

Related U.S. Application Data

[63] Continuation-in-part of Ser. No. 518,065, May 2, 1990, U.S. Pat. No. 5,016,643.

[51] Int. Cl.$^5$ ............................................. A61B 3/13
[52] U.S. Cl. ................................. 128/745; 351/221
[58] Field of Search ................. 128/745, 691, 637; 351/209, 210, 226, 221, 246; 356/28, 39

[56] References Cited

U.S. PATENT DOCUMENTS

| | | | |
|---|---|---|---|
| 4,166,695 | 9/1990 | Hill et al. | 356/28 |
| 4,425,924 | 1/1984 | Riva et al. | 128/745 |
| 4,443,075 | 4/1984 | Crane | 351/209 |
| 4,476,878 | 10/1984 | Riva et al. | 128/745 |
| 4,520,816 | 6/1985 | Schachar | 606/4 |
| 4,569,354 | 2/1986 | Shapiro et al. | 128/745 |
| 4,848,897 | 7/1989 | Aizu et al. | 351/221 |
| 4,856,891 | 8/1989 | Pflibsen | 351/210 |
| 4,883,061 | 11/1989 | Ziemer | 128/745 |
| 4,952,050 | 8/1990 | Aizu et al. | 351/221 |
| 5,016,643 | 5/1991 | Applegate et al. | 128/745 |
| 5,035,500 | 7/1991 | Rorabaugh et al. | 351/226 |

FOREIGN PATENT DOCUMENTS

| | | | |
|---|---|---|---|
| 02996 | 9/1991 | WIPO | 128/745 |
| WO91/16857 | 11/1991 | WIPO | 128/745 |

OTHER PUBLICATIONS

Laatikainen et al., "Capillary-Free Area of the Fovea with Advancing Age," *Invest. Ophthalmol. Visual Sci.,* (1977) 16(12):1154–1157, published in USA.

Bresnick et al., "Abnormalities of the Foveal Avascular zone in Diabetic Retinopathy," *Arch. Ophthalmol.,* (1984) 102:1286–1293, published in USA.

Bligard et al., "Aging Changes of the Parafoveolar Vasculature: A Trypsin Digest Study," *Invest. Ophthalmol.,* (1984) ARVO abstract only, published in USA.

Weale, "Why Does the Human Retina Possess a Fovea," *Nature,* (1966) 212:255–256, published in Great Britain.

Dartnall and Thomson, "Retinal Oxygen and Macular Pigmentation," *Nature* (1949) 164:876, published in Great Britain.

Bird and Weale, "On the Retinal Vasculature of the Human Fovea," *Exp. Eye Res.,* (1974) 19:409–417, published in Great Britain.

Yeung et al., "New Observations on Retinal Microcirculation at the Posterior Pole in Man," *Trans. Fourth Asia–Pacific Congress of Ophthal.,* (1973) 24:155–161, place of publication unknown.

Kluxen and Wilden, "An Entoptic Test in Diabetic Patients," *Diabetes Care,* (1987) 10(6):800–801, published in USA.

(List continued on next page.)

*Primary Examiner*—George Manuel
*Attorney, Agent, or Firm*—Arnold, White & Durkee

[57] ABSTRACT

Described herein are a range of techniques and apparatuses used to study the retinal vasculature near the fovea, a description of the need and rationale for noninvasive in vivo monitoring of the retinal vasculature, a presentation of theoretical and practical considerations which demonstrate that entoptic visualization of the smallest capillaries near the fovea is optimized by a short wavelength source of light which is constrained to enter the eye through a small limiting aperture moving in space near the eye at an optimized velocity in a circular or irregular path, and a discussion of the feasibility of using these techniques in a museum or novelty device as well as a research and clinical tool.

85 Claims, 19 Drawing Sheets

OTHER PUBLICATIONS

Helmholtz, "Treatise on Physiological Optics," Dover Publications, Inc., New York, New York, James P. C. Southall, Ed., (1962), 217–218, vols. I and II, published in USA.

Shimizu and Ujiie, "Structure of Ocular Vessels," (1978), 1–14, 16, 18 and 43, published by Igaku-Shoin, published in Japan.

Sharpe, "A Fresh Approach to Stabilized Retinal Images," *Physiological Society*, Part II, (1971) 217:9–10, published in Europe.

Macular Photocoagulation Study Group, "Argon Laser Photocoagulation for Neovascular Maculopathy," *Arch. Ophthalmol.*, (1986), 104:694–701, published in USA.

Macular Photocoagulation Study Group, "Argon Laser Photocoagulation for Ocular Histoplasmosis," *Arch. Ophthalmol.*, (1983) 101:1347–1357, published in USA.

Macular Photocoagulation Study Group, "Argon Laser Phtocoagulation for Idiopathic Neovascularization," *Arch. Ophthalmol., (1983) 101:1358–1361, published in USA.*

Macular Photocoagulation Study Group, "Krypton Laser Photocoagulation for Neovascular Lesions of Ocular Histoplasmosis," *Arch. Ophthalmol.*, (1987) 105:1499–1507, published in USA.

Han et al., "Visual Loss after Successful Photocoagulation of Choroidal Neovascularization," *Ophthalmol.*, (1988), 95:1380–1389, published in USA.

Zeffren et al., "Retinal Fixation Point Location Within the Foveal Avascular Zone," In Press, *Invest. Ophthalmol. and Visual Sci.*, published in USA.

Applegate et al., "Entoptic Visualization of the Retinal Vasculature Near Fixation," In Press, *Invest. Ophthalmol. and Visual Sci.*, published in USA.

Campbell and Robson, "A Fresh Approach to Stabilized Retinal Images," *Proceedings of the Physiological Society*, (1961), pp. 11P–12P, published in Great Britain.

Koppenberg et al., "An Entoptic Method for the Measurement of Eccentric Fixation in Amblyopia Ex Anopsia," *American Journal of Optometry and Archives of American Academy of Optometry*, (1972), 49(5), published in USA.

Medina et al., "Entoptic Visualization of Foveal Vessels," *ARVO Abstract Invest. Ophthal. Vis. Sic.*, (1986) 27(Suppl.):256, published in USA.

Bradley et al., "Psychophysical Evaluation of Retinal Vessels," *Noninvasive Assessment of the Visual System, 1989 Technical Digest Series, Vol. 7.*, Feb. 13–15, 1989, Santa Fe, New Mexico, published in USA.

Sinclair et al., "Blue Field Entoptic Phenomenon in Cataract Patients," *Arch. Ophthalmol.*, (1979) 97:1092–1095, published in USA.

Yap et al., "Psychophysical Measurement of the Foveal Avascular Zone," *Ophthal. Physiol. Opt.*, (1987) 7(4):405–410, published in Great Britain.

Applegate and Bonds, "Induced Movement of Receptor Alignment Toward a New Pupillar Aperture," *Invest. Ophthal. & Visual Science*, (1981) 21(6):869873, published in USA.

Zeffren et al., "Psychophysical Evaluation of the Foveal Avascular Zone (FAZ) Size and Foveola Location," *Clinical Research/Visual Psychophysics, Abstract No. 79*, published in USA.

Sharpe, C. R., "The Visibility and Fading of Thin Lines Visualized by Their Controlled Movement Across the Retina," *J. Physiol.*, (1972) 222:113–134, published in Great Britain.

Illuminance Profile

Illuminance Profile

Illuminance Profile small vessel
Illuminance profile

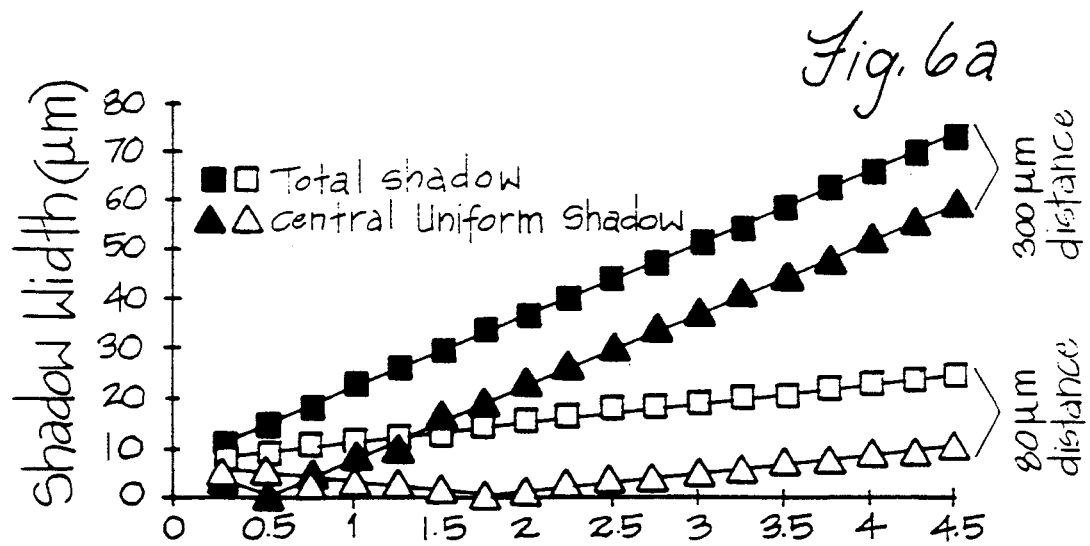
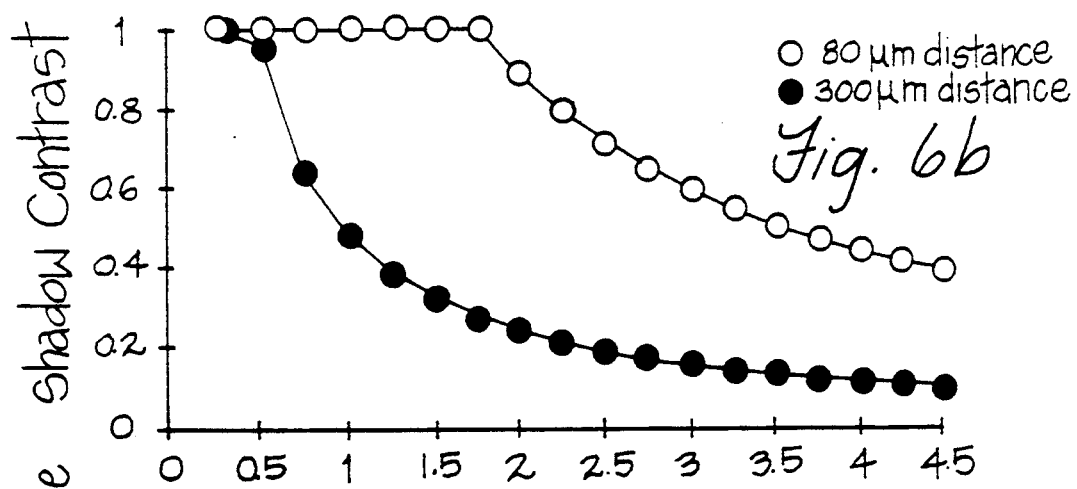
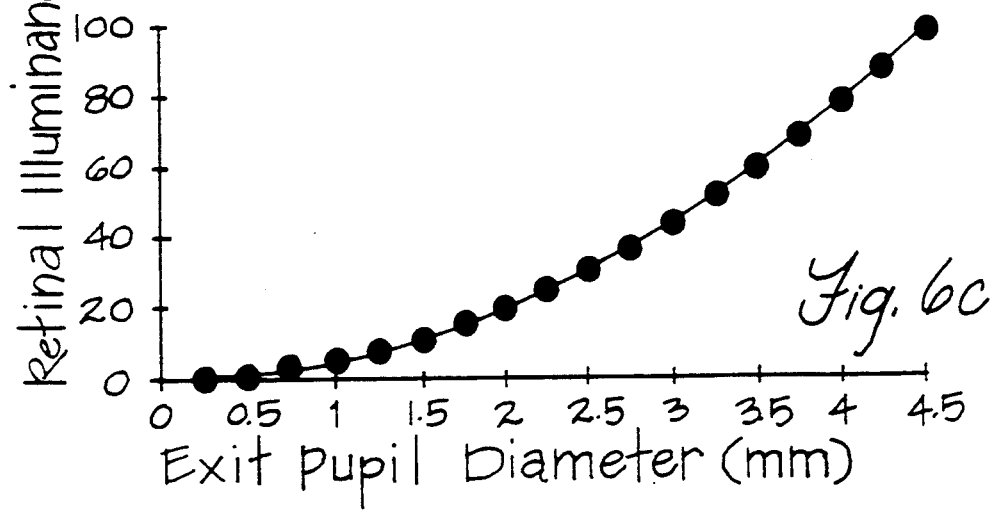

A TO $B_1$ = $B_1$ TO $PS_1$
FSM TO $B_2$ = $B_2$ TO SUBJECT
S TO $L_1$ = A TO $L_2$ = $L_2$ TO SUBJECT = 22 cm
$PS_1$ IS MOBILE
$PS_2$ IS STATIONARY

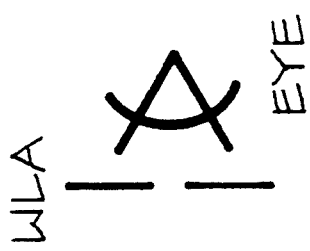 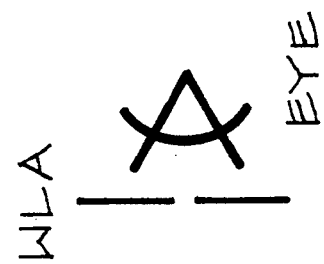
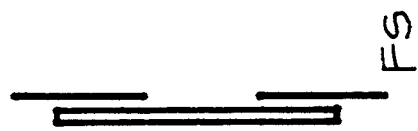 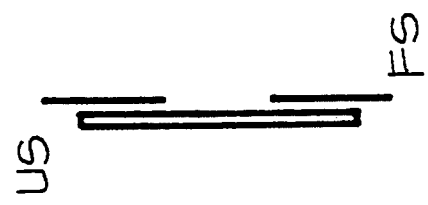
Fig. 15  Fig. 16

VIEW A UNIFORM FIELD

VASCULAR ENTOPTOSCOPE

Research relating to the development of the present invention was supported in part by grants from the United States Department of Health and Human Services (NIH EY08005 and EY07638). The United States government may have corresponding rights to the license and use of any resulting patent.

This is a continuation-in-part of U.S. Ser. No. 07/518,065 filed May 2, 1990.

GENERAL

The present application relates to a psychophysical method and apparatus for entoptically evaluating and mapping the human macula area vasculature with respect to the retinal point of fixation (RPF), as well as low-cost, simpler devices (i.e., no automatic hard copy provided) for self-visualization of the retinal vasculature or abnormalities thereof. Both mapping and simpler instruments incorporate similar principles and techniques as described herein to optimize the visual percept of the retinal vasculature and vascular abnormalities. In all embodiments of the Vascular Entoptoscope, light from a short wavelength source enters the eye through a small aperture, moving along a regular or irregular path at an optimized velocity. The essential difference between mapping and simpler instruments lies in the requirement to establish and monitor precise eye-instrument alignment and data display for accurate location of the RPF macular area retinal vascular defects.

MEDICAL APPLICATIONS

Knowing the precise location of the RPF is essential in modern ophthalmic surgery because the RPF can be inadvertently damaged during photocoagulation, resulting in marked vision loss. Unfortunately, the RPF is not visible on direct examination of the eye; its location must be determined subjectively and then related to observable landmarks. The present invention uses well-known techniques of entoptic visualization in a novel way to accomplish this goal.

A therapeutic trend in Ophthalmology is to photocoagulate (treat by burning) retinal abnormalities closer and closer to the retinal point of fixation (RPF). However, since treatment to the RPF can blind the eye, protocols advocate avoiding direct treatment to the RPF if at all possible. Since an examiner can not visualize the exact location of the RPF, protocols advocate using the center of the foveal avascular zone (FAZ) as a guiding landmark for RPF localization. That is, treatment should avoid the center of the FAZ on the assumption that the RPF is located at the center of the FAZ. Recent evidence using a mapping version of the Vascular Entoptoscope revealed that the RPF is not always centered within the FAZ (in fact not all eyes even have a FAZ). As a result, photocoagulation treatment in the foveal area may actually be causing blindness by burning the RPF unintentionally in about 20% of the cases where foveal area photocoagulation is the treatment of choice. This specific application of the Vascular Entoptoscope is discussed in detail in the section labelled "Alternative Methods and Prior Art" on page 10.

An important use for both precise mapping and simpler versions of the present invention will be in monitoring and treatment of diabetic retinopathy. Diabetes is the leading cause of blindness among working-age Americans, causing 8,000 new cases of blindness and 65,000 new cases of proliferative eye disease each year. In 50% to 84% of the cases, laser photocoagulation can prevent (or markedly reduce) adverse consequences of the proliferative stage of diabetic retinopathy. Receiving proper and timely treatment not only saves vision but reduces the socio-economic cost of diabetes-related visual impairment, currently estimated at $75 billion per year.

How is the Vascular Entoptoscope useful in the context of the diabetic? Current recommendations for medical care of diabetics include routine eye exams every 6 months to monitor the state of retinal vascular disease; however, many diabetics do not comply. If patients do not actually experience adverse effects (generally a visual acuity loss), many will assume nothing is wrong and conclude that a routine eye exam is a waste of time and money; this attitude can and often does lead to blindness. By the time a patient notices vision loss, significant damage has usually already occurred. Further, even for patients receiving regular care, the disease may progress undetected between appointments. Regular retinal examinations using the Vascular Entoptoscope, however, could alleviate these problems by allowing both convenient self-examination and more accurate and timely laser photocoagulation.

Why are regular exams so important and diagnostically significant for the diabetic patient and why is the Vascular Entoptoscope a significant improvement over current techniques? Regular eye exams are routinely performed because diabetes is a vascular disease and eye care specialists can monitor the vascular disease by directly observing the eye's vascular supply. In no other part of the body are working vessels so easily viewed without invasive procedures. The Vascular Entoptoscope will allow patients to monitor his or her own vessels down to the smallest $7\mu$ capillaries as often as they like. These capillaries are about ⅓ the size of the smallest vessels an eye care specialist can see by looking into the eye with an ophthalmoscope. Yet they are easily observed with the simpler embodiments of the present invention; sophisticated eye alignment systems are not required. Inexpensive (simpler) Vascular Entoptoscopes can thus be used in screening clinics or as take-home units, detecting the presence or absence of retinal vascular abnormalities (including changes in the size of the foveal avascular zone), which can then be evaluated more completely by a professional follow-up exam. If an abnormality is detected, the patient can approximately locate the vascular abnormality and direct the examiner's attention to that area. If treatment is warranted, the mapping Vascular Entoptoscope may be used to ensure maximum protection is given to the RPF.

MUSEUM APPLICATION

While our laboratory work at first focused on medical applications, the first potential buyer of a Vascular Entoptoscope was a museum. It was believed that seeing one's own smallest capillaries in a noninvasive fashion would be an excellent hands-on display that museum patrons would enjoy. In view of this, simpler versions of the device were designed as suitable for a museum environment (e.g., they do not contain sophisticated alignment and mapping systems). Such a device operates on the identical fundamental design principles of the more sophisticated Vascular Entoptoscope originally built.

NOVELTY APPLICATION

In developing the medical and museum applications as well as working with museum staff in developing the display, it became clear that if an inexpensive simple, hand-held, take-home device could be developed, it would not only have a significant medical market but would also have significant appeal as a novelty item. Therefore, we have attempted to reduce the physical embodiment of the fundamental design principles of the original vascular entoptoscope to simpler hand-held, low cost, take-home devices suitable for personal use and novelty markets.

DATA ON NORMAL PATIENTS

The Vascular Entoptoscope subsystem has been used to test normal and diabetic eyes. All subjects easily saw the Purkinje image of their retinal capillaries. Ten of the 14 normal subjects tested to date graphed details of the shadow of their FAZ in both eyes, and 2 (due to personal time constraints), in only one eye. Another subject observed a traditional FAZ in one eye, but saw capillaries running through what should have been the FAZ in the other; and one subject saw capillaries running through the fixation point in both eyes. FIG. 19 (a-d) depicts a sample of the variety of FAZ tracings obtained. FIG. 19a displays the tracing of one of only 3 eyes with a retinal point of fixation located in the geographic center of the FAZ as classically described anatomically. FIG. 19b displays a tracing from an eye with the retinal point of fixation located a typical distance from the geographic center of the FAZ, whereas FIG. 19c displays the tracing of the subject with the largest distance (189$\mu$) between the retinal point of fixation and the geographic center of the FAZ. FIG. 19d displays the tracing of one of 3 eyes with vessels in the retinal area more commonly occupied by the FAZ. Even by casual observation, it becomes clear that the FAZ boundaries are not always concentric with the fixation point (FIGS. 19b and 19c).

All 23 eyes with FAZs had retinal fixation points located within the FAZ. However, only three eyes from three different subjects had their retinal points of fixation located at the geographic center of the FAZ. Vectors defining the distance from the geographic center of the FAZ to the subject's fixation point and the direction of deviation (with 0° being horizontal to the right) were determined for each FAZ tracing. These distances were then converted to retinal distances using the Gullstrand reduced model eye with a nodal-point to retina distance of 16.67 mm after compensating for the optical magnification factor of the Maxwellian view optical system and the gain of the X-Y plotter. FIG. 20 shows use of a polar coordinate system to illustrate the location of the retinal point of fixation relative to geographic center of the FAZ for each eye tested. Note that while the data as a whole tends to cluster near the origin (i.e., the retinal point used for fixation tended to be nearer the center of the FAZ as opposed to the edge of the FAZ) the distribution of directions of deviation appear random. The largest deviation of the retinal point of fixation from the geographic center of the FAZ was 189$\mu$. The average deviation from the geographic center across all subjects is 66.50$\mu$. There was no tendency for the eccentricity of the retinal point of fixation to increase with increasing FAZ diameter.

This data indicate that the retinal point of fixation deviates from the geographic center of the FAZ by about 65$\mu$ (SD$\pm$50$\mu$) with a range of 0 to 190$\mu$. These findings suggest that laser burns centered on retinal points less than 300$\mu$ from the geographic center of the FAZ run a significantly higher risk than intended of falling directly on or nearer to the retinal point of fixation. Further, the risk of burning the point of fixation can markedly increase as burns are placed closer to the geographic center of the FAZ. The implications of this finding are profound and find support in current literature.

To illustrate, assume that, as in recent clinical trials, retinal lesions up to 200$\mu$ from the FAZ center are treated with burns which overlap the lesion by up to 100+$\mu$. Further, the data presented herein form a representative sample of the population for the location of the retinal point of fixation with respect to the geographic center of the FAZ (data points, FIG. 20). With these assumptions, 6 of 24 eyes (25%) have retinal points of fixation which are potentially vulnerable to being burned (FIG. 21, lightly shaded area). However, since photocoagulation treatment is generally limited to or slightly overlaps the area of frank pathology (e.g., neovascular membrane, histo-spot, etc.), it is likely that a series of burns will be placed only within the sector of the macular area containing the site of the lesion (FIG. 21, darkly shaded circles schematically show both a 200 and 100$\mu$ burn). Under these criteria and if the treatment sector of the macular area is limited to 90°, it is likely that for any one particular series of burns, one or two eyes out of our sample of 24 (4 to 8%) would have their retinal point of fixation adversely affected by photocoagulation therapy.

The obvious question arises as to what percentage of treatment failures (loss of 6 lines of visual acuity or more at first follow-up) can be accounted for by variations in the location of the point of fixation with respect to the geographic center of the FAZ. While this question cannot be definitively answered with the data collected to date, it is interesting to note that with argon laser treatment it has been reported that 9% of eyes treated for neovascular maculopathy (13), 9% of the eyes treated for macular area ocular histoplasmosis (14), and 10% of those eyes treated for macular area idiopathic neovascularization (15), lost 6 or more lines of visual acuity at first follow-up despite "successful" treatment of the pathology. Further, this order of magnitude of initial follow-up failure is not unique to argon treatment.

Studies using krypton laser therapy for histoplasmosis have reported a similar percentage of patients (8%) with a 6 line loss in visual acuity at first follow-up (16). The argument is further fueled by the fact that the best predictor of visual acuity loss despite adequate therapy is treatment proximity to the center of the FAZ (17). That is, when analysis is limited to eyes with lesions within 375$\mu$ of the FAZ center, between 8 and 33% of the eyes successfully treated lost 6 lines or more at first follow-up depending on the particular study. While this could be accounted for by assuming the lesions within 375$\mu$ are more likely to affect the retinal point of fixation, the data presented herein suggest another possibility. Given the uncertainties of thermal spread, dose specification, actual spot size in the plane of the retina, variation in pigment absorption and accuracy of burn placement with respect to desired location, the speculative estimate of 4 to 8% may indeed be an underestimate of the number of retinal fixation points at risk. Simply allowing for 50$\mu$ of uncertainty would raise the number of retinal fixation points at risk from 4 to 8% up to 16 to 20%. To the extent this analysis is correct, it suggests that therapeutic failures at first visit for eyes with retinal lesions between 200 and 375μ could be reduced by as much as 20% by using the actual retinal point of fixation as a reference as opposed to the geographic center of the FAZ.

In summary, the normal patient data collected using the Vascular Entoptoscope of the present invention indicate the retinal point of fixation is not always centered within the FAZ. Further, the deviations of the retinal point of fixation from the center of the FAZ can be large enough to jeopardize the retinal point of fixation during foveal area laser photocoagulation therapy which avoids the center of the FAZ as opposed to locating and avoiding the retinal point of fixation.

ALTERNATIVE METHODS AND PRIOR ART

Techniques to study the retinal vasculature can be classified into 3 categories: anatomic, angiographic, and psychophysical. Anatomic studies in human and other primates include whole mount and flat mount following trypsin digestion, and injection with India ink, neoprene latex and derivatives of methacrylic esters. While anatomic studies often provide eloquent detail of the vasculature surrounding the foveal area, they do not allow in vivo monitoring of changes in the vasculature and may be misleading. For example, latex injection under pressure may open anatomic connections which are not operative under normal physiologic conditions.

Fluorescein angiography, on the other hand, is generally accepted as the standard procedure for in vivo study of the human retinal vasculature, but it is invasive and not generally repeated daily or even weekly. Furthermore, to obtain the capillary detail necessary to study the FAZ and the vasculature near the fovea requires clear optical media and skilled photographic personnel. And even if photographic conditions are ideal, the angiographic detail of the foveal area vasculature may be variable in quality, depending on the density of the macular pigment and variations in normal fundus pigmentation.

Nevertheless, fluorescein angiography as well as angiography with other dyes have been used extensively to study the retinal vasculature and FAZ in both healthy and diseased eyes in vivo. Laatikainen and Larinkari (1) reported FAZ diameters around 0.57 mm for 167 eyes of 158 healthy patients (mean=0.572, range 0.23 mm to 0.83 mm). Bresnick et al. (2), in a study of the FAZ in diabetics, reported FAZ diameters between 0.58 and 1.00 mm with a mean of 0.73 mm for the normal control group (non-diabetic). Together these findings are consistent with the anatomic findings of Bligard et al. (3) where post-mortem human eye FAZ diameters were reported to range from 0.12 to 1.2 mm (mean 0.65 mm) using trypsin-digest. In diseased eyes, the FAZ has been reported to be smaller than normal in patients with cicatricial retinopathy of prematurity and larger than normal in vascular occlusive diseases such as diabetes, sickle cell retinopathy, talc embolic retinopathy and retinal branch vein occlusion. Taken together, all of these data provide a basis for comparison with retinal maps made possible by the psychophysical techniques of the present invention. Psychophysical procedures, however, can provide data unobtainable with angiography.

For example, even in the presence of cloudy ocular media, viewing a bright uniform blue field (430 nm) allows the entoptic visualization of leucocytes ("flying corpuscles") in the retinal capillaries surrounding the foveal area. Careful observation of the phenomenon reveals an area apparently centered on the RPF where no leucocytes are seen, presumably the FAZ. Yap et al. capitalized on this phenomenon to measure, in one eye of 22 normal subjects, FAZ diameters ranging between 1.92 and 2.86 degrees (0.59 to 0.83 mm on the retina assuming a secondary nodal point-to-retina distance of 16.67 mm). Earlier estimates using the same entoptic phenomena found the diameter of the FAZ to be approximately 1.5 degrees as measured in object space or 0.44 mm on the retina (Weale (4) quoted by Dartnall and Thomson (5)). But, while entoptic visualization of leucocytes provides a non-invasive method for making inferences about the FAZ and the vasculature of the foveal area, it does not provide a view of the retinal vessels themselves.

Direct entoptic visualization of the retinal vasculature can be achieved by allowing light to enter the eye from unusual or constantly varying angles. This effect, first noted by Purkinje in 1819 (6), is strikingly distinct and often spontaneously reported by patients during routine ophthalmoscopy. Bird and Weals (7), using both fluorescein angiography and entoptic visualization of the retinal vasculature by scleral trans-illumination, noted that not all normal individuals with excellent visual acuity have FAZs which are truly avascular. They point out that unless extreme care is taken during the entire photographic process, vascular details within the FAZ may not be imaged (or seen) with fluorescein angiography but are visible entoptically. These findings corroborate the earlier fluorescein angiographic work of Yeung et al. (8) and emphasize the potential sensitivity of entoptic viewing of the central retinal vasculature.

Clinically, entoptic visualization has long been used to help evaluate the functional status of the retina behind obstructed media. More recently it has been used as a guide to train eccentric fixators to improve fixation, and to study the normal variation in the size and shape of the FAZ. To the best of the present inventors' knowledge, only one study has used entoptic visualization to monitor an active disease state. Kluxen and Wilden (9) taught 136 insulin-dependent diabetics how to observe their retinal vasculature entoptically. In patients with 1-5 microaneurysms, as revealed by fluorescein angiography, 55% could entoptically detect their own pathology. In patients with 6-20 microaneurysms the percentage increased to 77%. In patients with greater than 20 microaneurysms with severe background and proliferative retinopathy, 90% could reliably detect their own pathology and many could document the appearance of new and disappearance of old microaneurysms over time.

While entoptic visualization of the retinal vasculature is impressive in its apparent detail, capturing this detail in a quantifiable manner is difficult. First, entoptic visualization is subjective by nature. Second, foveation of the variety of intricacies of the vascular detail is impossible because the entoptic image remains fixed with respect to the retina (i.e., the location of the retinal vasculature is fixed with respect to the photoreceptors; therefore, eye movements cannot foveate the vessel of interest). Together these effects have limited the usefulness of this phenomenon. To minimize these problems, the present invention optimizes the visual percept of the retinal vasculature by carefully selecting stimulus parameters. One way to present these optimized stimulus parameters is to use the optical principles of Maxwellian view. The use of Maxwellian view for entoptic visualization of the retinal vasculature was first alluded to by Helmholtz (10) in his *Treatise on Physiological Optics* where, in discussing entoptic visualization of the retinal vasculature, he said:

The . . . vascular figure may be seen also by looking through a compound microscope with nothing upon the stage, the background being the uniformly bright circular aperture of the diaphragm. When the eye moves to and fro a little at the ocular, the slender retinal blood vessels appear sharply delineated in the field, particularly those running at right angles to the direction of the motion, whereas the others vanish that are parallel to this direction.

Helmholtz goes on to point out the importance of the size of the Maxwellian view exit pupil on shadow formation by stating:

If the pupil is perfectly free, and the eye is turned towards the bright sky, every point of the pupillary plane may be considered as a source of light sending rays in all directions to the fundus of the eye, just as if the pupil itself were a luminous surface. The result is that the blood vessels of the retina project broad hazy shadows on the parts of the retina immediately behind them, the length of the umbra being only about four or five times the diameter of the blood vessel . . . Hence it may be assumed that the umbra of the vascular shadow does not reach the posterior surface of the retina at all. But when the light enters the eye through a narrow aperture in front of the pupil, the shadow of the blood vessel is necessarily smaller and more sharply defined, and since the umbra is longer, parts of the retina that were formerly partially shaded are now completely shaded, while other adjacent parts are not shaded at all.

Thus, the principles of entoptic visualization have been described, but prior to the present invention, no device had been built or proposed to optimize the patient's view of the retinal vessel pattern surrounding the RPF to detect retinal vascular defects and precisely locate the RPF in relation to the macular area retinal vasculature. The need for this information, however, is substantial and growing.

For example, as discussed above such data would be particularly useful for eye surgeons who, during photocoagulation therapy, focus high power laser beams on the retina by using the retinal vessels as landmarks. It is most important for the surgeon to avoid burning the retinal point of fixation (to avoid vision loss), but that point is subjectively determined by the patient in all cases and cannot reliably be assumed to lie at the center of the FAZ or the anatomical fovea. Thus, the present invention fills an important need and provides a significant safety factor for the increasing number of patients who could benefit from foveal area photocoagulation therapy.

ORIGIN OF THE ENTOPTIC VISUAL PERCEPT OF THE RETINAL VASCULATURE

Within the portion of the retina resting on the choroid (pars optica), several layers can be distinguished; FIG. 1 shows them schematically. At the posterior pole, the distribution of retinal components is altered to form highly specialized structures which maximize visual acuity, the anatomical fovea and foveola. In the center of the fovea, the inner retinal layers down to the outer nuclear layer are displaced, forming a pit, the foveola, which contains the highest density of cones in the retina (147,000 cones per square mm). The retinal capillaries of the area of the fovea typically form concentrically arranged channels ending in a capillary loop approximately 0.5 mm across which outlines a capillary-free zone, the FAZ. The lateral displacement of inner retinal structures, including the retinal vasculature, presumably exists to leave an unobstructed light path to the site of phototransduction, thereby enhancing image quality.

In a normal observer, visual performance is maximized at the subject's point of fixation. That is, when asked to fixate a point in space, normal observers move their eyes such that the point of interest is imaged on the retinal region providing the highest resolution. The connection between fixation and optimal resolution, together with the histological specialization of the retina, suggest that a normal individual will move the eye to place the image of the RPF on the foveola. Thus the RPF and the foveola are commonly assumed to be coincident and reasonably centered in the FAZ. But, experimental use of the present invention has brought this assumption into sharp question for a significant minority of patients. Using the methods and apparatus taught herein, these patients may be identified and their treatment appropriately modified to maximize preservation of vision. The guideposts in this process are vascular shadows subjectively perceived by the patient and their relationship to the RPF.

Since the retinal vasculature lies anterior to the photoreceptors, shadows of the vasculature are cast in the plane of the photoreceptors. Under normal viewing and lighting conditions the vascular shadows of all but the largest vessels have low contrast and all are effectively stabilized with respect to the photoreceptors. Since patterns which are stabilized in the plane of the receptors fade and become invisible, vascular shadows are not perceived under normal lighting and viewing conditions.

Entoptic visualization of the vascular shadows can be achieved by increasing shadow contrast and breaking shadow stabilization. Contrast can be increased by placing a small light source in the eye's entrance pupil and shadow stabilization can be broken by changing the retinal angle of incident light by constantly moving the light source. There are at least four characteristics of the vessel shadow pattern in the plane of the entrance aperture of the photoreceptors which will affect shadow visibility: 1) the width of the shadows; 2) the contrast of the shadows; 3) the spacing of the shadows; and 4) the speed and path of shadow movement. In the present invention, the first goal was to define the stimulus parameters which optimize these characteristics and render the vascular bed surrounding the fovea easily visible.

The present invention includes stationary or portable (e.g. hand-held) apparatuses for self-visualization of the retinal vasculature (often referred to as a simpler device), as well as apparatuses and methods for entoptically perceiving and precisely mapping the foveal area vasculature of a human subject's retina (mapping apparatus). The precise mapping apparatus comprises a means to establish and maintain the translational and rotational alignment of said eye with said apparatus which would be necessary for accurate mapping, whereas the simpler devices do not require an alignment means.

Alignment may be achieved by means of an affixed bite bar, preferably of dental impression-type material, for a subject to orally embrace, or a chin rest, an alignment ring and monitoring system. Numerous eye tracking systems could also be modified and employed to meet this instrumentation need. Both the precise mapping device and the simpler devices include a means for directing light into the eye resulting in the angle of illumination of said eye's retina changing with time. Practically this is accomplished by directing short wavelength light into the eye through a narrow aperture moving in space near the eye at an optimized velocity in a circular or irregular path.

The most practical way to meet these design objectives in a real instrument is to constrain the light to enter the eye through a small moving exit pupil.

The precise mapping apparatus has a main light source (preferably of variable intensity and shape) which is imaged in or near the entrance pupil plane of the eye (to form the small moving exit pupil of the apparatus) and a means of moving said main light source or image of the main light source along a path in space. The main light source has a peak wavelength of about 430 to 555 nm (preferably about 470 nm) and a half band pass of approximately ±60 nm. The exit pupil is preferably circular and has a diameter of approximately 0.5 to 3 mm (preferably 1.0 mm or less). The exit pupil of the device is imaged between or near said eye's entrance pupil plane and anterior focal plane. The main light source image is preferably of uniform intensity. This main light path is preferably circular and 2 to 6 (more preferably 4 mm) in diameter. The main light path is retraced at a rate of 0.5 to 10 Hz (preferably 3.5 Hz). There are several ways to image the main light source to form the exit pupil of the device. This can be accomplished with lenses or mirrors or a combination of both.

Also in the apparatus are means to image an aperture at optical infinity or any other plane of interest (e.g., to correct for refraction error of the subject) as an optical field stop for said apparatus. This can be accomplished with lenses or mirrors or a combination of both. This aperture may be of variable size and shape and preferably is an iris diaphragm.

The apparatus additionally may have a luminous or nonluminous fixation point (this is particularly important in the precise mapping device but not necessarily important in the simpler devices) and a means to form an image of the fixation point on the retina of the eye. The fixation point retinal image is within (preferably centered) the limits of the field stop. This can be accomplished with lenses, or it can be done with mirrors, or a combination of both.

A luminous or nonluminous tracking point and means to form an image of the tracking point on the retina of said eye may also be part of the apparatus. Such a tracking point is particularly important for the precise mapping device. When a tracking point retinal image is used, a means of moving said tracking point retinal image with respect to the fixation point is required. This can be a simple mechanical means of physically moving the point or, as in the precise mapping apparatus, a device such as a joystick or similar x-y controller. Imaging the tracking point onto the retina can be accomplished with lenses or mirrors or a combination of both. In addition, in some applications it may be advantageous to have the fixation and tracking point sources be dots on a CRT (computer screen). This would provide several advantages in documentation as well as serving as a means for creating the comparator for blood flow measurements.

An important apparatus component of the precise mapping apparatus is a means of transducing movement of the tracking point retinal image to yield coordinates of its present location on retina with respect to the location of the fixation point retinal image. The location can be kept track of using several different methods. In principal, it is only necessary to correct for the optics of the eye and apparatus. This can be done using a computer or mechanical and/or optical methods. The tracking point retinal image coordinates are calibrated in units of length measured on said retinal surface or units of angular subtense.

To achieve the desired results, the precise mapping apparatus includes a means of compiling or displaying coordinates of the tracking point retinal image movement. Depending on the user's desires, computer programs can be written by those skilled in the art to compile and display the tracking light location in any manner desired. This compilation or display comprises a map of the tracking point retinal image positions with respect to the fixation point retinal image.

The precise mapping apparatus also includes a means to detect and indicate magnitude and direction of translation of the eye with respect to the apparatus. There are numerous eye tracking systems which could be modified and employed to meet this instrumentation need. This indication of magnitude and direction of translation of the eye with respect to said apparatus is visible or is sensed by an external operator or computer.

The precise mapping apparatus of the present invention for entoptically perceiving and mapping the foveal area vasculature in the retina of a human subject's eye may also be modified for concomitantly studying white blood cell circulation through the retinal vasculature. In such modification, the apparatus also comprises a blue-field light source and a means to illuminate the retina with the blue-field light source. This blue-field light source is preferably of variable intensity. For this purpose, the modified apparatus further comprises a speed-comparator light source for casting an image and a means to form a retinal image of the speed-comparator light on the retina. This speed-comparator light source is preferably of variable intensity and the speed-comparator light source retinal image a size about equal to entoptically perceived white blood cells.

Additionally, such a modified apparatus includes a means of causing said speed-comparator light retinal image to move along a path having a variable length and curvature on the retina at a fixed velocity.

Lastly, the modified apparatus includes a means of rotating and translating the speed-comparator light retinal image on the retina. This, and the immediate means are of types commonly known to those of skill in this area.

The blue-field light source has a characteristic wavelength of about 430 to 500 nm, is directed coaxially with light from the fixation light source, comprises approximately 50% of total light, and is applied to said retina constantly or intermittently at a frequency of about 50 to 60 Hz.

The retinal path of the speed-comparator light image is straight or curved to mimic the course of a retinal vessel and has a length of about $10^{-4}$ to $10^{-3}$ m. The velocity of the speed comparator can be adjusted to mimic velocity of a white corpuscle passing through vasculature.

The present method for entoptically perceiving and/or mapping the macular area retinal vasculature of the human eye regardless of apparatus embodiment may be described as follows. The perception of the retinal vasculature is optimized by a short wavelength source of light (430 to 555 nm) which is constrained to enter the eye through a small aperture (0.5 to 3 nm) moving in space near (or optically in) the eye at an optimal velocity (30 to 60 mm/sec) in a circular (diameter 2 to 6 mm) or irregular path (contained in a circle between 2 and 6 mm in diameter).

This method for entoptically perceiving and mapping the foveal area vasculature in the retina of the eye of a human subject under examination with respect to the retinal point of fixation may be modified to perceive white blood circulation. The modified method includes illuminating the retina intermittently or constantly with a blue-field light source of variable intensity and, if intermittent, having a duty cycle of less than 100%. The subject reports perceived entoptic perception of said white blood cell circulation within the capillaries. The subject adjusts the intensity of the light sources for best entoptic perception.

The present invention embodies an apparatus for entoptically perceiving the macular area retinal vasculature of the human subject's eye under examination. This apparatus comprises a light beam source and a means of directing a light beam from said source into a subject's eye at angles such that the angle of illumination of said eye's retina with the light beam changes with time. The light beam from said source is variable in intensity and shape. The light beam source may be a light generator such as a bulb or a light field which has been narrowed through a constraining aperture.

In another embodiment, the present invention involves an apparatus for the above purposes which comprises a means of directing a light beam into a subject's eye at angles such that the angle of illumination of said eye's retina by the light beam changes with time. In one preferred embodiment the light beam may be varied in intensity and shape. Additionally, a means to image an aperture at optical infinity or other plane of interest as an optical field stop for the apparatus is included. This aperture may be of fixed or variable size and shape. The aperture referred to above is preferably that of an adjustable iris diaphragm.

In yet a slightly more complex embodiment, the present apparatus comprises a means for directing a light beam into the eye at angles such that the angle of illumination of the eye's retina changes with time; a means to image an aperture at optical infinity or other plane of interest as an optical field stop for the apparatus, the aperture may be of fixed or variable size and shape. The optical field stop is movable and luminous or nonluminous. Lastly with this embodiment, a luminous or non-luminous fixation point with a means to image said fixation point on the retina of the eye is added. The field stop is preferably sectionalized to facilitate location of vessels and/or vessel defects with respect to the fixation point.

In any of the embodiments of the present invention, a means may be provided to correct for refractive error of the eye being examined. In one preferred embodiment, the light beam is directed in a circular path 2 to 6 mm in diameter. A preferable diameter is about 3.5 mm and is approximately centered in the eye's pupil. The light beam may additionally be directed in an irregular path over an area having a dimension of about 2 to 6 mm such that all angles of retinal illumination obtainable with a circular path are present. The light beam according to this embodiment of the present invention is preferably to be traced at the rate of 0.5 to 10 Hz. The light beam may be directed in an irregular path as a series of random illuminations in an area of dimension of about 2 to 6 mm. Substantially all angles of retinal illumination obtainable with a circular path should also be present with such a random or irregular light beam pattern. The fixation point or the image of the fixation point is generally centered within an area of retinal illumination. Preferably the area of retinal illumination is a circle and the fixation point is centered approximately within said circle. The wavelength of the light beam is preferably of a wavelength between about 430 to 550 nm and has a half band pass of 0 to 100 nm. The light beam has a preferred peak wavelength of about 470 nm and a half band pass of ± about 60 nm. The constraining aperture through which the light beam is directed into the eye is preferably about 0.1 to 3 mm diameter. The light beam is preferably directed to the eye through a constraining aperture, this being the exit pupil of the device. The constraining aperture may be of irregular shape with a greatest dimension of 0.1 to 3 mm. A preferable limit for this constraining aperture is about 1 mm. The constraining aperture is imaged between the eye's retina and the eye's anterior focal plane. It is possible that the light beam itself could be a broad light source or field which is stationary and the constraining aperture is moving, for example, rotating, to direct a beam at the differing angles into the eye. The light beam is preferably diffuse and of uniform intensity.

The most sophisticated embodiment of an important aspect of the present invention is an apparatus for entoptically perceiving and mapping the macular retinal vasculature of a human subject's eye under examination. This apparatus comprises: (a) a means to establish and maintain translational and rotational alignment of said eye with said apparatus; (b) a light source of variable intensity illuminating an aperture which is imaged in or near the eye's entrance pupil plane to form an exit pupil of the apparatus and a means of moving said exit pupil along a path in space; (c) a means of imaging said exit pupil into said eye's entrance pupil at angles such that the angle of illumination of an illuminated area of said eye's retina changes with time; (d) a means to image an aperture stop at optical infinity or other plane of interest to correct for any refractive error as an optical field stop for said apparatus, said aperture being of variable size and shape; (e) a luminous or nonluminous fixation point and a means to image said fixation point on the retina of said eye; (f) a luminous or nonluminous tracking point and a means to form an image of the tracking point on the retina of the eye; (g) a means of moving said tracking point retinal image with respect to said fixation point retinal image; (h) a means of transducing movement of said tracking point retinal image to yield coordinates of its location on said eye's retina with respect to said fixation point retinal image; (i) a means of compiling or displaying coordinates of said tracking point retinal image movement, said compilation or display comprising a map of tracking point retinal image positions with respect to said fixation point retinal image; and (j) a means to detect and indicate magnitude and direction of translation of said eye with respect to said apparatus.

In this latter apparatus the tracking point may be a light source. The means to establish and maintain rotational alignment is preferably a bite bar for the subject to orally embrace or a chin and forehead rest. The movement of the apparatus exit pupil is circular, preferably about 2 to 6 mm in diameter and approximately centered in the eye's pupil. A most preferred diameter is about 4 mm. The path of the light beam is preferably retraced in a circular path at a rate of about 0.5 to 10 Hz. A more preferred retracing rate is about 3.5 Hz. The aperture stop in this apparatus is preferably an adjustable iris diaphragm. The light source has a peak wavelength of about 430 to 555 nm and a half band pass of 0 to 100 nm, a preferred wavelength being about 470 nm and preferred half band pass of ± about 60 nm. The exit pupil of the apparatus is preferably circular with a diameter of 0.1 to 3 mm, more preferably 1.0 mm or less. The exit pupil of the apparatus is preferably imaged in or near the eye's entrance pupil plane. An indication of magnitude and direction of translation of the eye with respect to the apparatus described in step (j) is preferably visible. This indication, also in step (j), is preferably sensed either by an external operator or by a computer monitored sensor. The tracking point retinal image coordinates described in step (h) may be corrected manually for retinal image translation caused by translation of the eye with respect to the apparatus. The retinal image coordinates of step (h) may be corrected by automatic computation for retinal image translation. The coordinates described in step (i) are generally calibrated in units of length measured on the retinal surface or in units of angular subtense. The means of moving the tracking point retinal image as described in step (h) is preferably a joy stick or similar x-y controller.

Additionally, white blood cell circulation through the retinal vasculature may be monitored, in addition to mapping the vasculature, by utilization of the above-described device along with a blue-field light source with the means to illuminate the retina with this blue-field light source. In conjunction with this, a luminous or nonluminous speed comparator in a means to form a retinal image of the speed comparator on the eye's retina may be included. This speed comparator retinal image is of a size about equal to the entoptically perceived white blood cells. A means of causing the speed comparator retinal image to move along a fixed or variable path on the eye's retina and at a fixed or variable velocity is also included. This coincides with a means for rotating and translating the speed comparator retinal image. The blue-field light is applied to the retina constantly or intermittently in alternation with the light source of step (a) at a rate which minimizes perceptual flicker and has a duty cycle variable to optimize perception of both the retinal vessels and the white blood cells.

FIG. 1 is a schematic illustration of the location of vessels (solid ovals) within the various layers of the retina. Inner limiting membrane (ILM), neural fiber layer (NFL), ganglion cell layer (GCL), inner plexiform layer (IPL), outer plexiform layer (OPL), outer nuclear layer (ONL), outer limiting membrane (OLM). Direction of light entering the eye is from top of diagram to bottom.

Figure 4A:
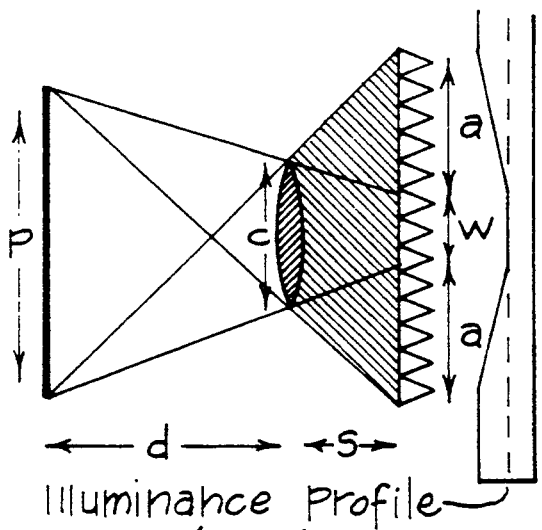
Figure 4B:
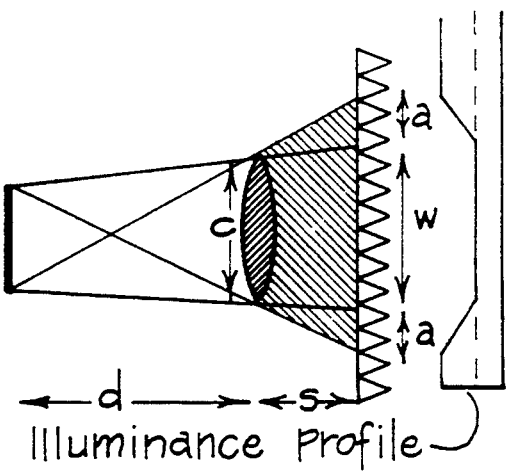
Figure 4C:
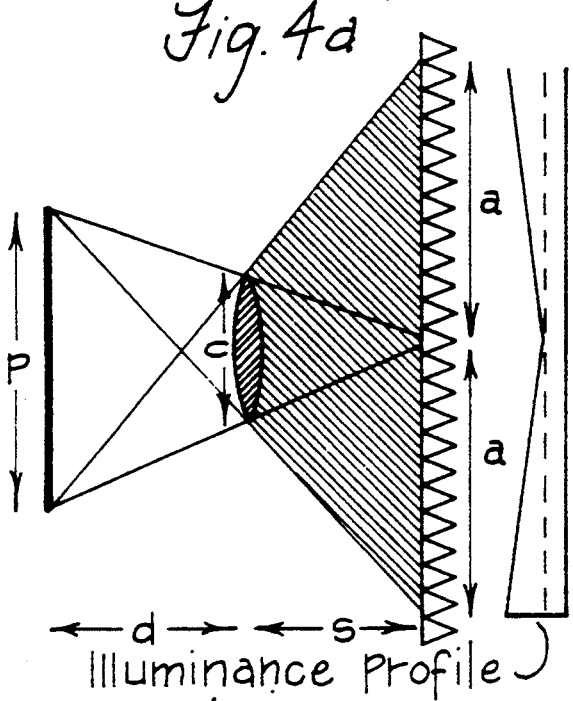
Figure 4D:
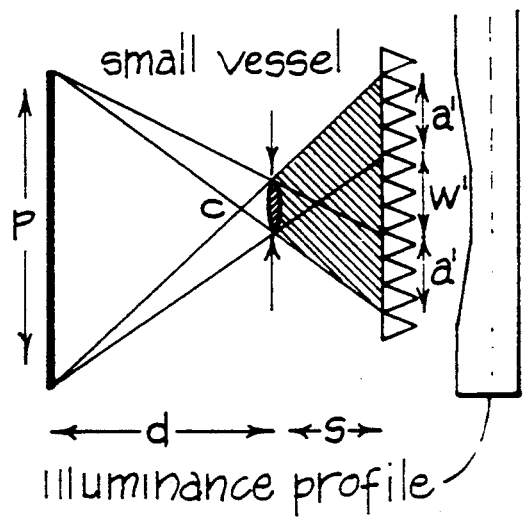

FIG. 4a–4d shows schematics illustrating the interaction of size of the constraining aperture (exit pupil of device) and vessel location and size, on the illuminance profile of the vessel shadow in the plane of the entrance aperture of the photoreceptors. "P" denotes the diameter of the constraining aperture in this case imaged in the exit pupil of the eye, "w" represents the uniform portion of the illuminance profile having maximal contrast (umbra), "a" illustrates the penumbra portion of the shadow (ramping illuminance profile) and w' represents the portion of the shadow with a uniform illuminance profile of less than maximal contrast. Parameters c, d, s and w are defined in FIG. 2. FIG. 4a is used as a reference to illustrate the effects on the vessel shadow in the plane of the photoreceptors of decreasing the size of the source P (FIG. 4b), increasing the distance s (FIG. 4c) and decreasing the vessel size c (FIG. 4d).

Figure 5:
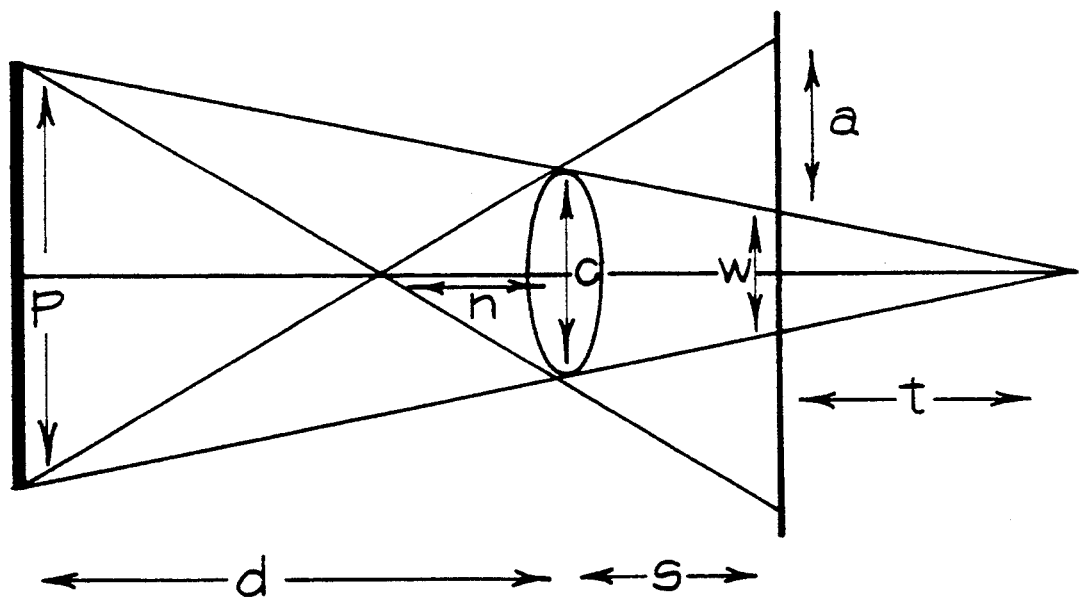

FIG. 5 is a schematic diagram purposely distorted to illustrate the geometric relationships of shadow formation which define shadow width and the nature of the illuminance profile. Parameters defined in FIGS. 2 and 4.

FIGS. 6a–6c shows predictions of the effect of diameter of the constraining aperture (exit pupil of device) on shadow width (FIG. 6a), shadow contrast (panel b) and retinal illuminance (FIG. 6c) for 7 micron capillaries positioned at the ILM (300 microns distance) or at the INL (80 micron distance).

Figure 7A:
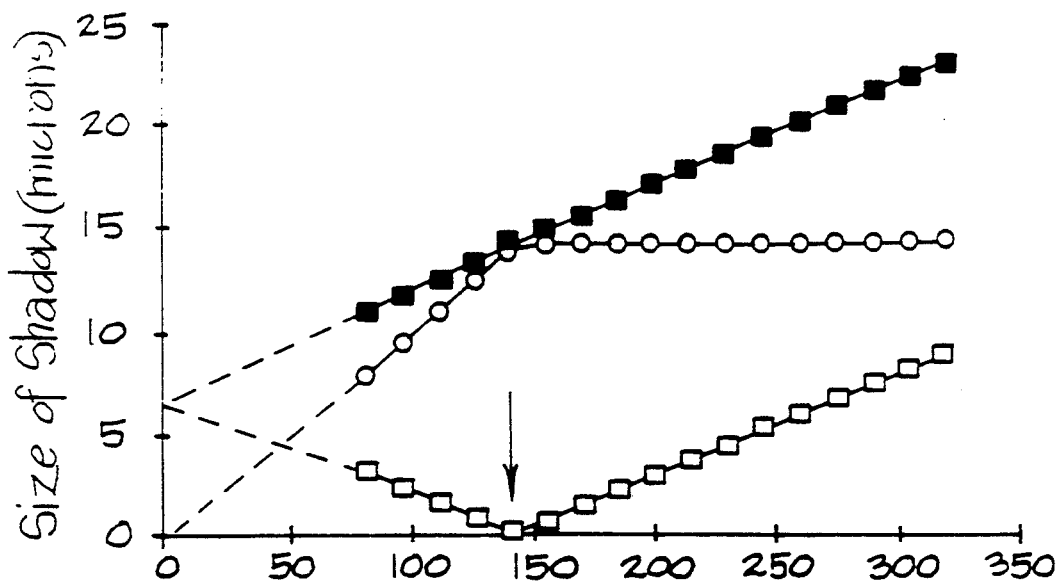
Figure 7B:
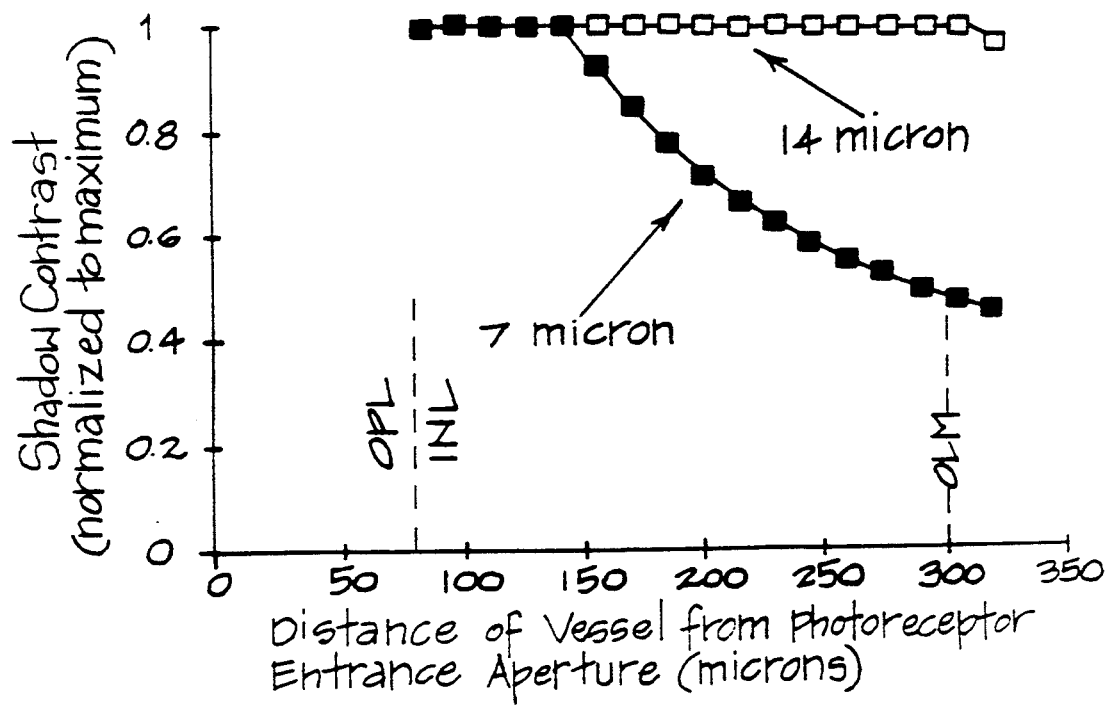

FIG. 7a–7b, FIG. 7a illustrates total shadow width (solid squares) as well as the width of the uniform (open squares) and ramping (open circles) portions of the shadow formed by a 7 micron capillary as a function of vessel location; FIG. 7b shows normalized shadow contrast for a 7 micron (solid squares) and 14 micron (open squares) capillary as a function of vessel location. Retinal layers OPL, INL and OLM refer to the outer plexiform layer, the inner nuclear layer and the outer limiting membrane, respectively.

Figure 8:
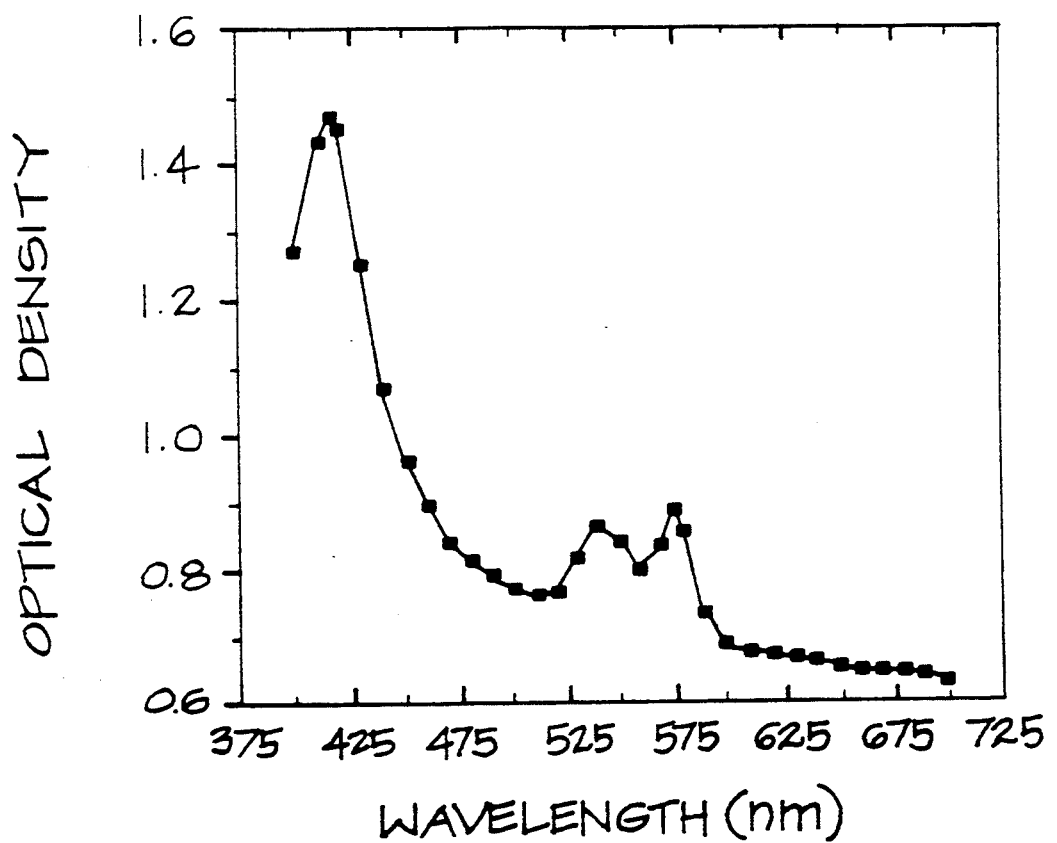

FIG. 8 shows the optical density of whole blood (subject RAA) diluted 500 times through a pathlength of 1 cm as a function of wavelength.

Figure 9A:
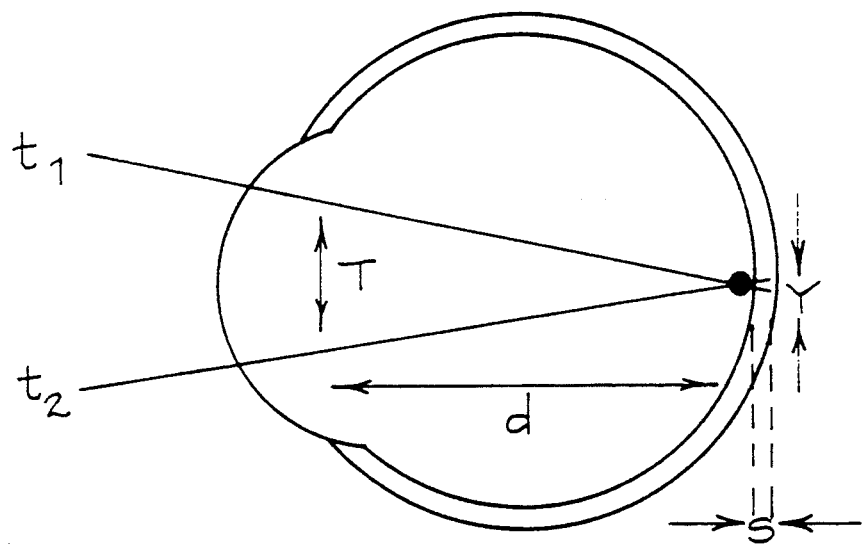
Figure 9B:
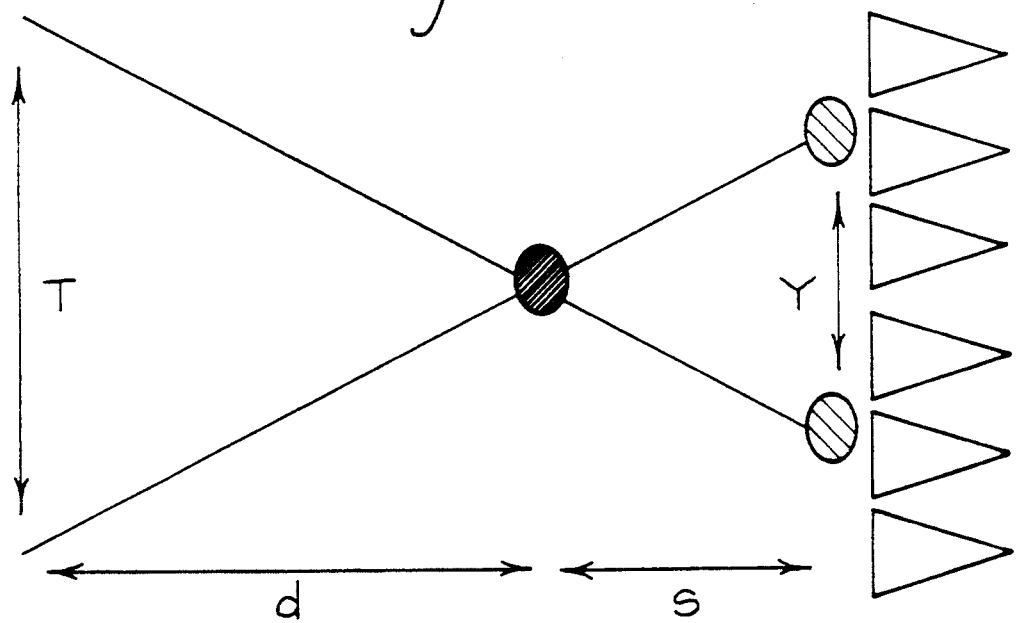

FIGS. 9a–9b, panel a shows vessel shadow movement y induced by movement T of a small source in the plane of the eye's exit pupil; FIG. 9b exaggerates the scale to illustrate the effect.

FIGS. 10a–d, illustrates maximum shadow movement perpendicular to the long axis of the vessel induced by a small source rotating along a circular 4 mm diameter path in the plane of the eye's entrance pupil as a function of vessel distance from the photoreceptor entrance aperture.

Figure 11:
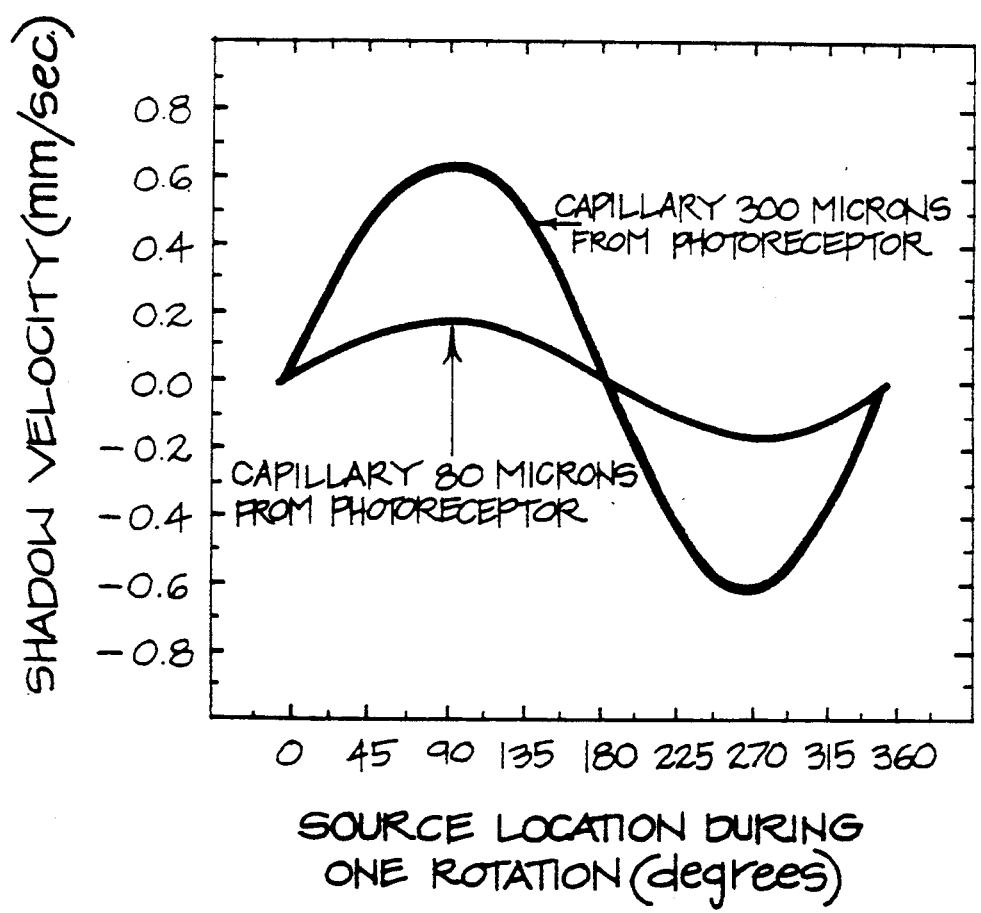

FIG. 11 shows shadow velocity perpendicular to the long axis of the vessel at the plane of the entrance aperture of the photoreceptors resulting from a small source rotating along a circular 4 mm diameter path in the plane of the eye's pupil as a function of source location.

Figure 12:
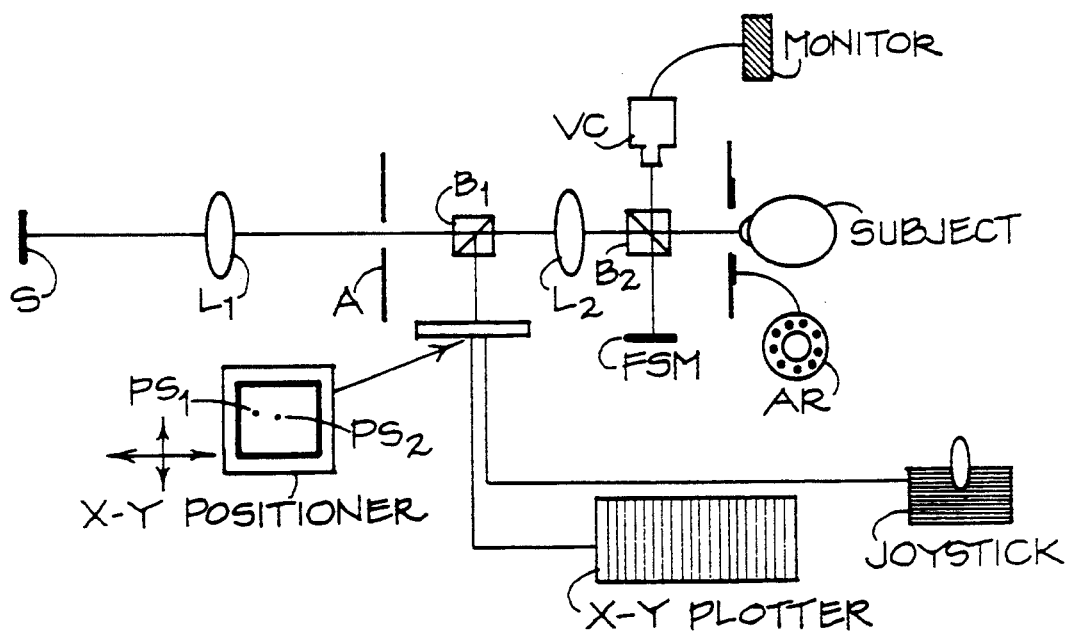

FIG. 12 is a schematic representation of the mapping Instrument. S: source, a rotating 1 mm pinhole for the Vascular Entoptoscope sub-component and a stationary centered pinhole for the Blue Field Entoptoscope sub-component; $L_1$: collimating lens; A: variable iris diaphragm; $B_1$: beam splitter; $L_2$: Maxwellian view lens; $B_2$: beam splitter; VC: video camera; AR: alignment ring; $PS_{1\&2}$: point sources.

FIGS. 13 through 17 describe devices (termed simpler), which are designed to optimize the percept of the macular area retinal vasculature by using the same operating principles described for the mapping instrument.

Figure 13:
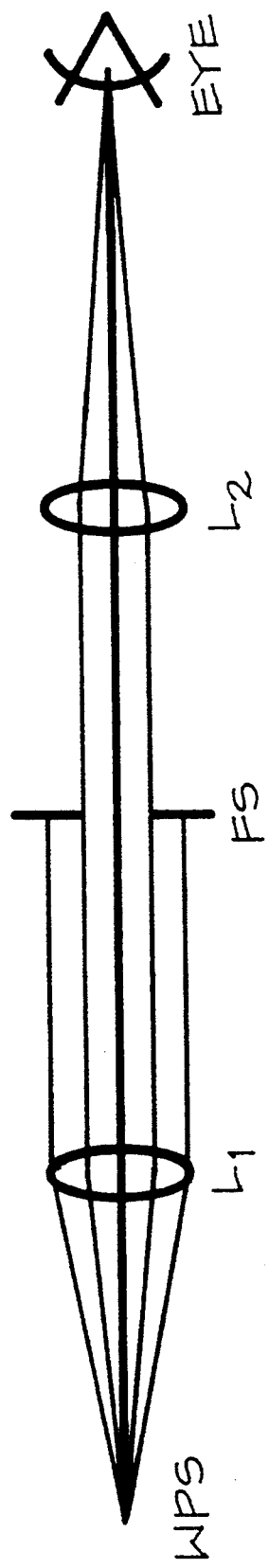

FIG. 13 illustrates schematically a simpler Vascular Entoptoscope which has a small wobbling short wavelength point source (WPS) which is constrained to enter the eye through a small aperture by imaging the source near the pupil of the eye using two lenses ($L_1$ and $L_2$). The field of view over which vessels can be seen is defined by the field stop (FS).

Figure 14:
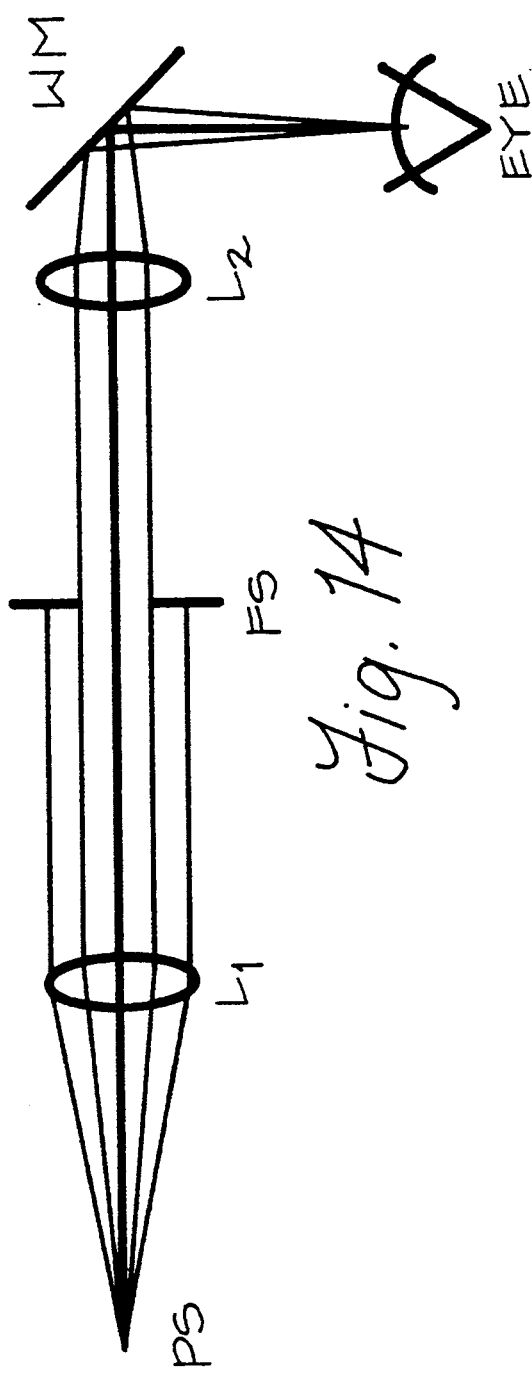

FIG. 14 illustrates schematically a device that is in principle similar to the device illustrated in FIG. 13, except that movement of the source image is induced by a wobbling mirror (WM).

FIG. 15 illustrates schematically a second way the fundamental operating principles of the simpler Vascular Entoptoscope can be achieved. Here a uniform short wavelength source (US) back illuminates a field stop (FS) which defines the field of view over which vessels can be seen. Here light is constrained to enter the eye through a small wobbling limiting aperture (WLA).

FIG. 16 illustrates schematically a device that is similar in principle to the device illustrated in FIG. 15 except that no provision is made within the device for seeing the borders of the field stop clearly.

Figure 17:
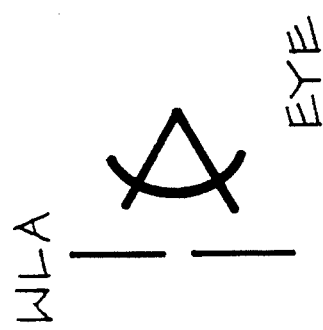

FIG. 17 illustrates schematically the simplest configuration of the operating principles of the Vascular Entoptoscope. Here the user simply views a uniform source preferably of short wavelength such as the sky through a small wobbling limiting aperture (WLA).

Figure 18:
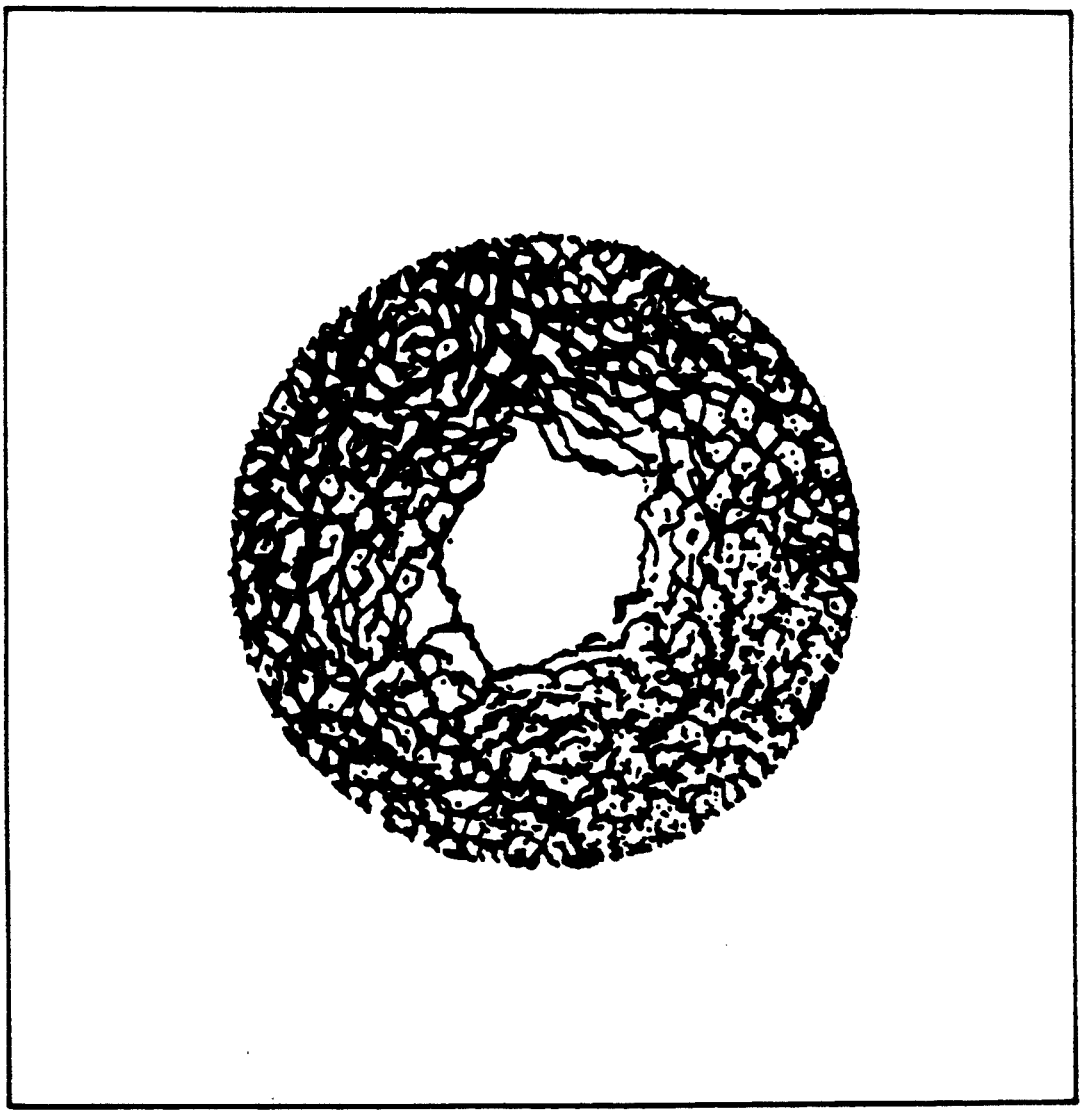
Figure 19A:
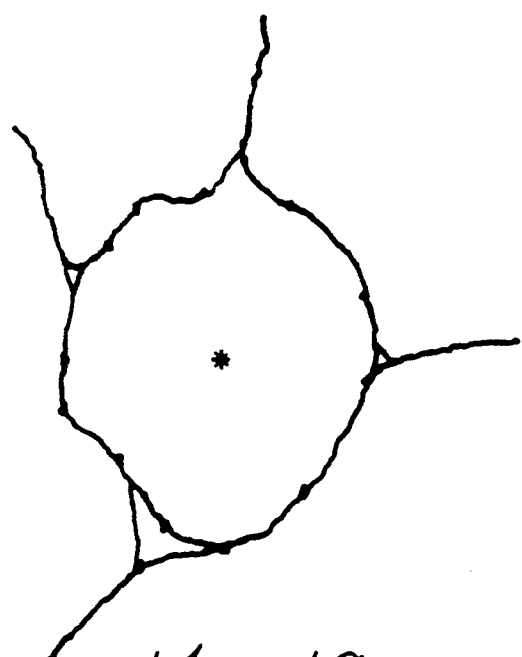
Figure 19B:
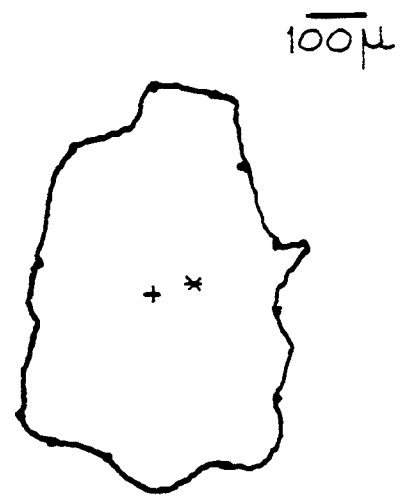
Figure 19C:
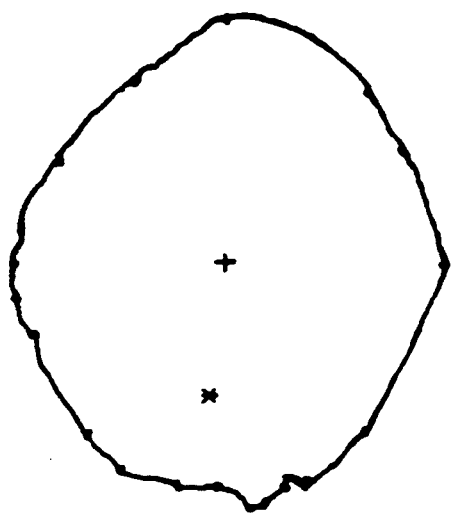
Figure 19D:
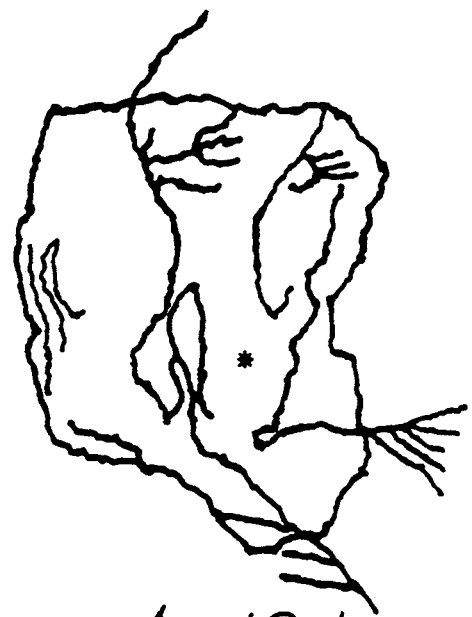

FIG. 18 shows a simulation of entoptic percept of the macular area retinal vasculature.

FIGS. 19a–19d describes four FAZ tracings. FIG. 9a: Classic FAZ tracing with centered fixation point; FIG. 9b: FAZ tracing showing a typical eccentric location for the retinal point of fixation; FIG. 9c: FAZ tracing showing a large eccentric distance between the geographic center of the FAZ and the retinal point of fixation; FIG. 9d: Tracing showing no FAZ and retinal capillaries near the retinal point of fixation. *=center of fixation; +=geographic center of FAZ.

Figure 20:
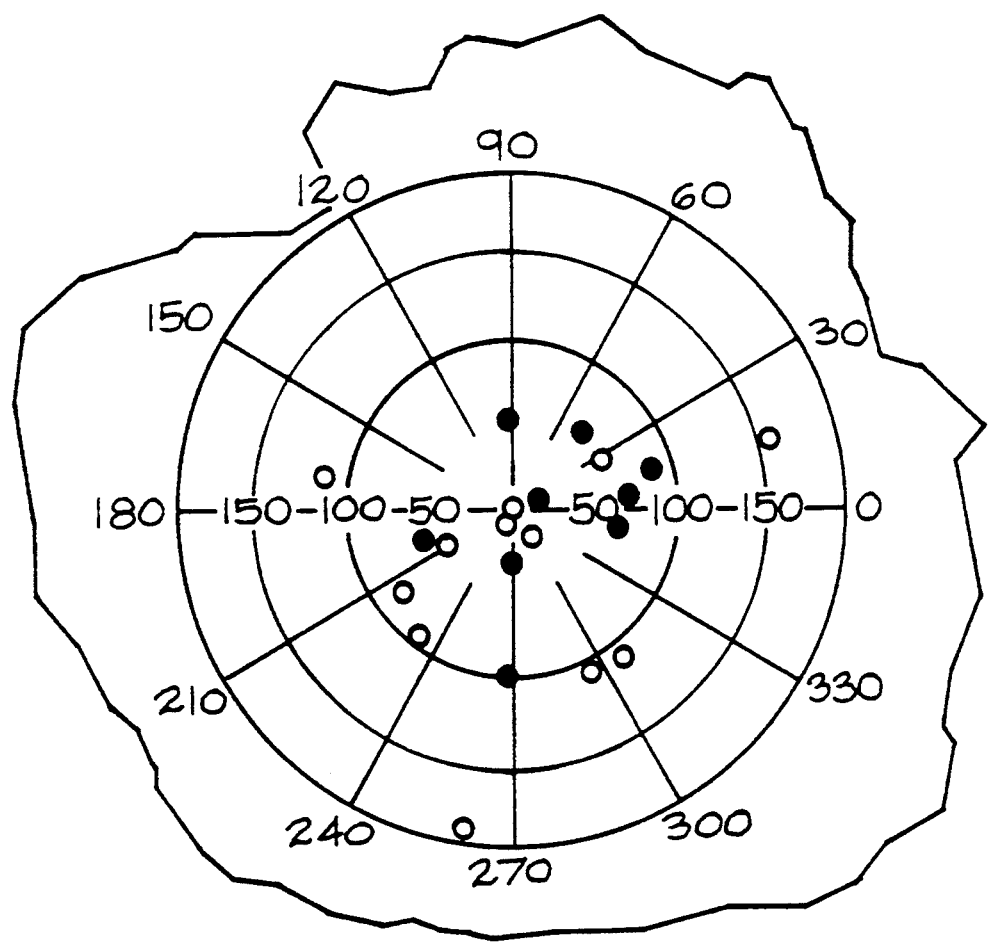

FIG. 20 illustrates location of the retinal point of fixation from the geographic center of the FAZ tracing for each eye tested in a study using the precise mapping Vascular Entoptoscope. Left eyes, open circles; right eyes, closed circles. Irregular circular pattern represents a typical FAZ border. Units: Angles in degrees, distances in microns.

Figure 21:
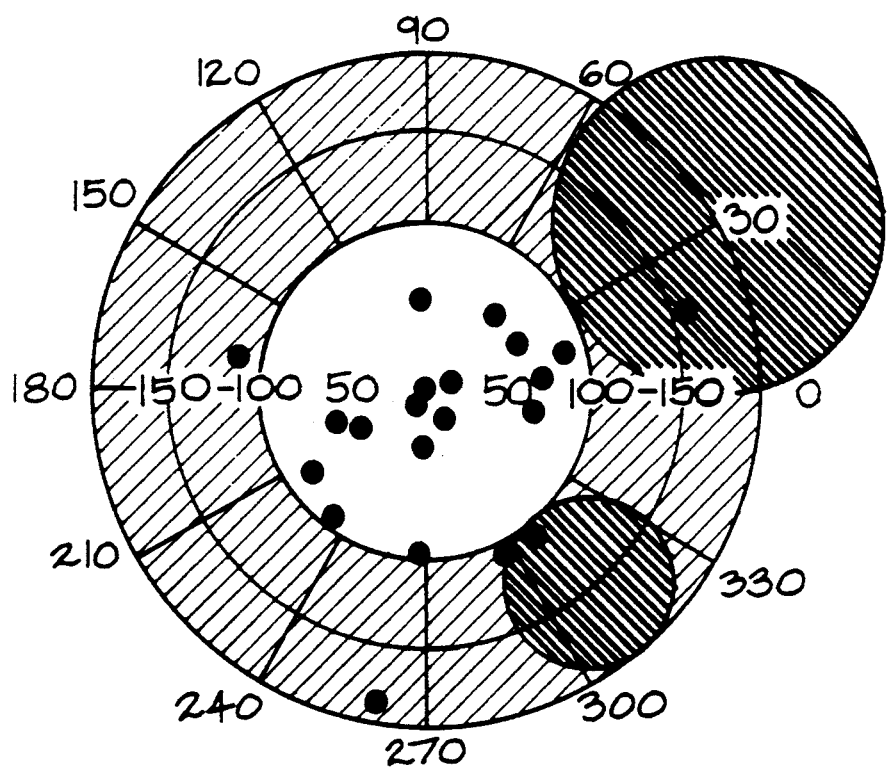

FIG. 21 demonstrates location of the retinal point of fixation (solid dots) from the geographic center of the FAZ tracing for each eye tested. Lightly shaded area represents the area at risk of damage from a single 200$\mu$ or 100$\mu$ laser burn (darkly shaded circles) placed to overlap a lesion 200$\mu$ from the center of the FAZ by 100$\mu$.

MODELING ASSUMPTIONS

While a full treatment of the optical properties of the retinal blood vessels would deal with absorption, focusing, and scattering by the blood vessel walls, the blood plasma, and the individual red and white corpuscles, as well as diffraction effects, an excellent description of the entoptic perception of the macular area retinal vessels may be provided using a model based on absorption and the geometric optics of shadow formation. Therefore, for the present model the optical consequences of focusing, scattering and defraction are ignored in favor of a model based on absorption and geometric optics.

1. Shadow Width

Using geometrical optics, shadow width as seen at the photoreceptor entrance aperture, here defined to be the outer limiting membrane (FIG. 2), depends on four key elements: 1) the width of the vessel, c; 2) the distance from the vessel to the entrance aperture of the photoreceptor, s; 3) the distance from the illumination source to the vessel, d; and 4) the size of the source illuminating the vessel, P.

1.1 Vessel Width.

Detailed histological data from human eyes provide estimates of diameter for arteries (100 microns), veins (180 microns), arterioles (21 microns), venules (23 microns), and capillaries (7 microns). Shimizu and Ujiie (11) contend that capillaries may be slightly larger at the border of the foveal avascular zone (10 to 15 microns).

1.2 Distance from the Vessel to Photoreceptors.

Figure 1:
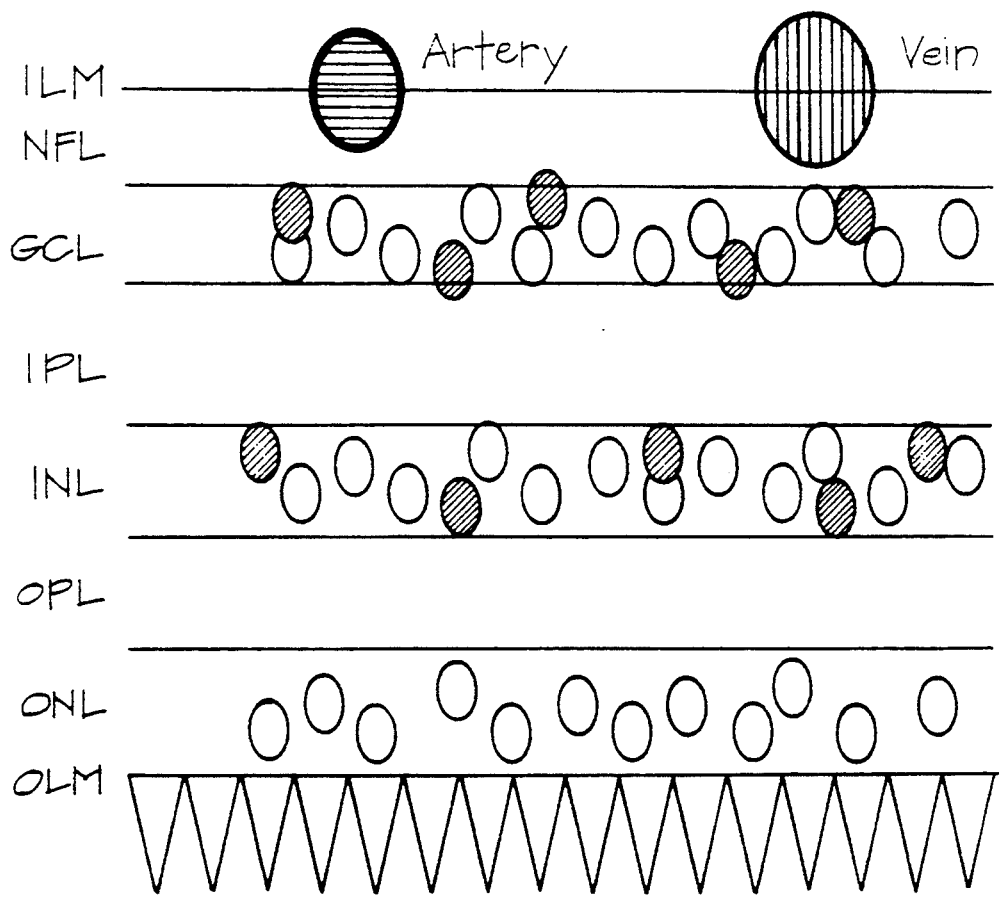

In general, the major arteries, veins, arterioles and venules lie in the nerve fiber layer (NFL), and the capillaries are distributed from the inner limiting membrane (ILM) down into the inner nuclear layer (INL) (FIG. 1). However, the precise distribution of the capillaries is controversial. It has been suggested that they are either evenly distributed or that they are concentrated in two laminae. Despite the disagreement over the precise distribution of the capillaries, collectively these reports set the range of the distribution of vessel location as the ILM and outer plexiform layer (OPL) border. Therefore, around the foveal region, the retinal vessels will be considered to lie between 300 and 80 microns from the entrance aperture of the photoreceptors. Hereafter, for readability the entrance aperture of the photoreceptors will be referred to simply as the photoreceptors.

1.3 Constraining Aperture (exit pupil of instrument) Distance.

The exact distance from the constraining aperture or image thereof to the vessels (d in FIG. 2) is not important in determining shadow size in cases where the distance d is considerably larger than the distance s from the vessels to the photoreceptors. Nevertheless, to calculate accurately the width of the vascular shadows for a variety of capillary locations, the distance d needs to be defined for each capillary location. This can be done by defining the location of the constraining aperture (exit pupil of the device) and adopting the optical parameters of a schematic eye. If the eye is assumed to be Gullstrand's simplified schematic eye and the eye's iris (the aperture stop of the eye) is placed on the anterior surface of the crystalline lens, then the distance from the eye's exit pupil to the photoreceptors is 20.49 mm (FIG. 3). Combining these assumptions with the knowledge that distance from the capillaries to the photoreceptors ranges from 80 and 300 microns, the distance d varies from 20.410 mm for capillaries at the INL to 20.190 mm for capillaries in the ILM. Given these parameters, and assuming the constraining aperture is a point in the plane of the entrance pupil, the retinal shadows of the vessels will have a rectangular illumination profile and, at the outer limiting membrane, will be slightly wider (0.4–1.5%) than the vessels themselves. Alternatively, if we had placed the constraining aperture at the anterior focal point of the eye, then light after refraction by the eye would be collimated and the shadows cast would be the same width as the vessels.

Figure 2:
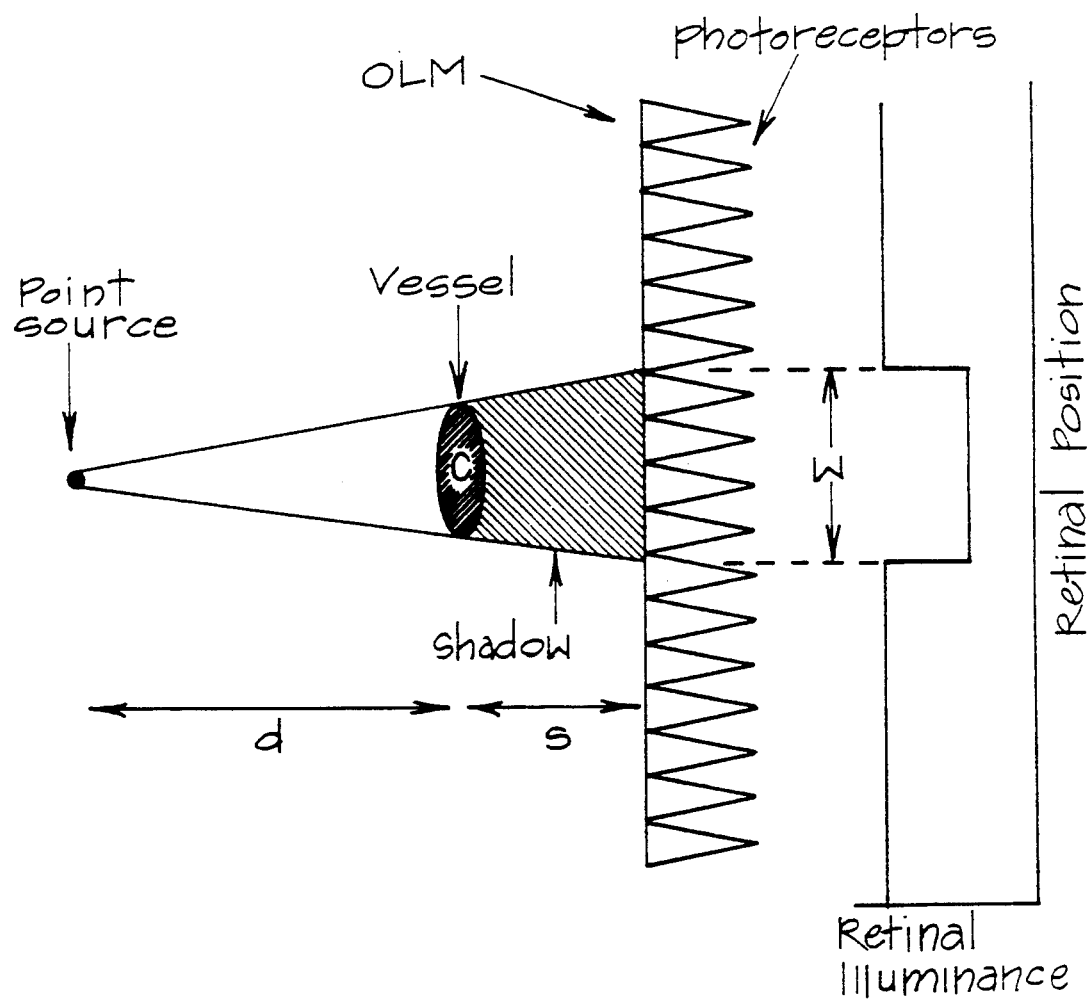
FIG. 2 is a point source illumination of a vessel c from a distance d forming a shadow with a rectangular illuminance profile of maximal contrast with a width w in the plane of the photoreceptor's entrance aperture assumed to be the outer limiting membrane (OLM) a distance s from the capillary.
Figure 3:
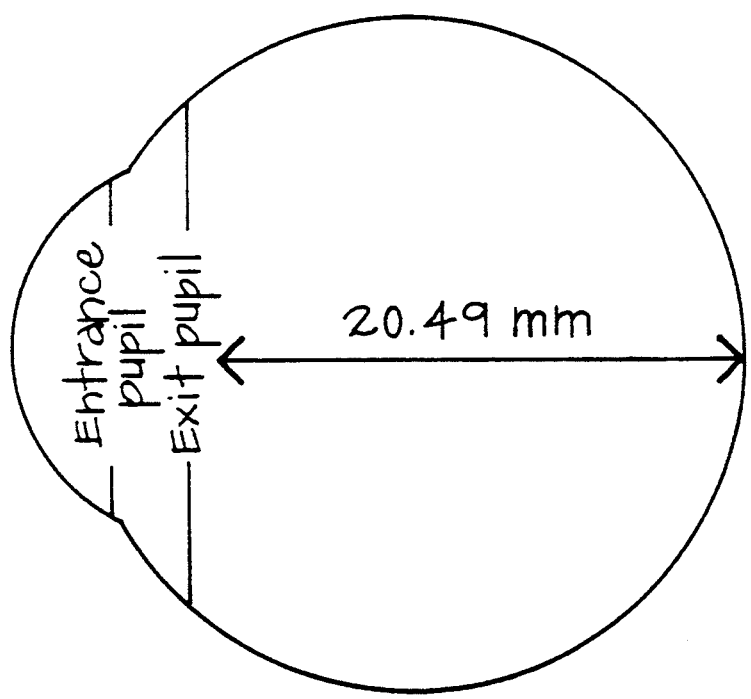
FIG. 3 shows the location of the entrance pupil of the eye with respect to the corneal apex and location of exit pupil of the eye.

By similar triangles in FIG. 2, the shadow width (w) in the point-source case is given by $$\text{width of shadow} = w = (s+d)c/d$$

where c is vessel diameter. It is clear from this analysis that the shadow from the smallest capillaries (7 microns) is larger than the diameter of one photoreceptor (approximately 2 microns). Unfortunately, a point source considerably smaller than 7 microns is difficult to create. If the source is large compared to the size of the vessel, which is so in any real apparatus, then the illuminance profile of the shadow is no longer rectangular.

1.4 Size of the Constraining Aperture (exit pupil of device).

When the constraining aperture has a finite diameter P, there is in general an umbra, a region of total shadow (darkly shaded area in FIG. 4), and a penumbra, a region in which the source is partly eclipsed by the vessel (lightly shaded). The illuminance profile in the shadow may or may not contain an area of total shadow (umbra) in the plane of the photoreceptors (FIG. 4). When an umbra is present in the plane of the photoreceptors, (FIG. 4a and 4b illuminance is at a minimum over a central uniform area, then increases through the penumbral regions. As P or s increases, or c or d decreases, the width of the umbra in the plane of the photoreceptors can decrease to zero (FIG. 4C). As a further change in this direction is made, by further increasing source diameter P for instance, no photoreceptor will be hidden from the entire source by the vessel. However, a region of uniform illuminance will again appear (FIG. 4D). This region is less darkened than the actual umbra, and its illuminance will approach that of the background as P continues to increase. Using similar triangles (FIG. 5), the width of the umbral region w in the case where the constraining aperture has real area and cannot be modeled by considering the constraining aperture a point source is given by $$w/t = c/(s+t) = P/(d+s+t)$$

$$w = (Pt)/(d+s+t)$$

and the width of the penumbra on each side of the central uniform area a is given by $$a/s = p/d$$

$$a = Ps/d$$

Small changes in the diameter of the constraining aperture P in the plane of the pupil will have a marked influence on shadow width, shadow contrast and mean retinal illuminance. FIG. 6 illustrates these three points. FIG. 6a displays the variation in the total width of the shadow (squares) and the width of the central uniform portion of the shadow (triangles) as a function of the diameter of the constraining aperture (exit pupil) for a 7 micron capillary located either 300 (solid symbols) or 80 microns (open symbols) from the receptors. Notice in FIG. 6a that while the total shadow width (squares) is always greater than the width of a foveal cone (approximately 2 microns) and increases monotonically with source diameter, the width of the uniform portion of the illuminance profile (triangles) first decreases and then increases with constraining aperture diameter. The initial decrease in the width of the uniform portion of the illuminance profile corresponds to the umbra portion of the shadow moving anterior to the plane of the photoreceptors. At the point where the uniform portion of the illuminance profile goes to zero and starts to increase, maximum contrast of the shadow begins to decay. These effects of exit pupil size on image contrast are illustrated in FIG. 6b for a 7 micron capillary located either 300 microns (closed circles) or 80 microns (opened circles) in front of the photoreceptors. Examination of FIG. 6b reveals that increasing the exit pupil size beyond 0.5 mm will reduce shadow contrast for the smallest capillaries near the ILM (300 micron distance); however, shadow contrast will remain high for larger vessels or for those capillaries located nearest to the photoreceptors until the source diameter exceeds 1.75 mm. FIG. 6c illustrates the typical limitation of most systems. That is, for a constant luminance, reductions in constraining aperture area (i.e., a decrease in the size of the exit pupil of the optical system) produces proportional reductions in retinal illuminance. For a circular exit pupil, retinal illuminance will be inversely proportional to $r^2$. Thus a tradeoff exists. Decreases in the beam constraining aperture will increase shadow contrast but decrease retinal illuminance. The former will increase the contrast of the shadow and the latter will decrease the retinal sensitivity to contrast.

Given these three considerations, shadow width, shadow contrast and retinal illuminance, combined with a desire to keep the worst case shadow contrast at least 5 times threshold (see shadow contrast below), the constraining aperture diameter P was set at 1 mm for modeling purposes.

FIG. 7a illustrates the width of 1) the uniform portion (open squares), 2) the ramping portion (open circles), and 3) the total width (solid squares) of the illuminance profile in the plane of the photoreceptors as a function of vessel distance from the photoreceptors. There are several important points illustrated by this figure. First, notice the total shadow width (solid squares) of the 7 micron capillary increases as the distance of the vessel from the photoreceptor increases. Second, and more importantly, notice the width of the shadow having a uniform illuminance profile (open squares) at first decreases to zero and then increases. Like FIG. 6a, the decreasing portion of this function reflects the gradual movement of the umbra to a position anterior to the photoreceptor. Further increases in vessel distances (greater than approximately 140 microns) produce increases in the width of the central uniform section of the illuminance profile. As the width of the uniform section of the illuminance profile increases, the illuminance of this section increases and lowers shadow contrast (FIG. 7b). The width of the ramping portion of the shadow (open circles, FIG. 7a) at first increases as the uniform portion decreases to zero and then remains essentially constant as the capillary to photoreceptor distance continues to increase. Although this analysis demonstrates that total shadow width for the smallest capillary is always considerably bigger (>10 microns) than a photoreceptor (2 microns), it does not indicate whether or not there is sufficient total contrast or if the spacing of shadows is adequate for perception.

2. Contrast of the Shadows

As illustrated in FIG. 7b, the relative shadow contrast is affected by vessel size and position. As can be seen, the use of a small 1 mm diameter constraining aperture (exit pupil) ensures a full contrast shadow for all but the smallest vessels positioned near the ILM.

Vessels larger than 15 microns will always have a portion of the umbra in the plane of the photoreceptors. The lowest contrast expected for 7 micron capillaries positioned 300 microns from the entrance aperture of the photoreceptors (worst case situation) using a 1 mm exit pupil is approximately 50% of the maximum contrast achievable. Now the question becomes, is this contrast reduction sufficient to render the shadow of these small capillaries invisible? To answer this question the actual contrast of the shadow must be determined.

Bird and Weale (7) have discussed this issue and, estimating hemoglobin absorption for white light in small capillaries to be 40% (transmission 60%), they calculate log $\Delta I/I$ to be $-1.6$ (or a contrast of 2.5%). Using the same estimate of hemoglobin transmission, we calculate a maximum shadow contrast of 40% $[(1-0.6)/(1)]$. Thus a 7 micron capillary 300 microns in front of the photoreceptor entrance aperture experiencing a 50% reduction in contrast should have a contrast of approximately 20%. Larger exit pupils (greater than 1 mm) will further decrease the shadow contrast of the small 7 micron vessels (FIG. 6b) and expand the range of vessel widths affected with a contrast loss. Smaller exit pupils (less than 1 mm) will increase the contrast of the smaller vessels and decrease the range of vessel widths affected with a contrast loss. This analysis helps to explain why trans-scleral illumination with a source such as a penlight or illuminator (which presumably becomes even larger due to scatter within the sclera) does not provide an easily visible entoptic view of the foveal capillaries.

The contrast of the vascular shadows can be increased further for any sized exit pupil by limiting the spectral output of the source of light to the absorption peak for blood and, in particular, hemoglobin. FIG. 8 illustrates the optical density for a 1 cm optical pathlength of the blood of one of the inventors (RAA) diluted 500 times as a function of wavelength. As can be seen from this figure, blood has its maximum optical density (absorption) in the visible spectrum at 415 nm which corresponds with the maximum density for oxyhemoglobin. Given the wavelength of maximum absorption for deoxyhemoglobin is 430, limiting the spectral output of 1 mm diameter exit pupil to a band between 415 and 430 will increase the shadow contrast of a 7 mm capillary from 20% to approximately 45% [i.e., 1.47 (optical density of whole blood diluted 500 times at 415 nanometers)+2.7(correction for 500 times blood dilution)−3.15(correction for 1 cm measurement thickness to 7 micron capillary thickness)=1.02; as a result, transmission through the capillary will be approximately 9.55% of the incident light creating a contrast of $(1-0.0955)/(1)=90.45\%$ in the umbra (which lies in front of the photoreceptors in the case of the 7 micron capillary) and 45.23% in the plane of the photoreceptors].

While a short-wavelength narrow-band source (415 to 430 nm) theoretically provides the best retinal contrast, practically, as a result of the lower sensitivity of the middle and long wavelength sensitive cone mechanisms to short wavelength light, the reduced spatial resolution of the short wavelength sensitive cone mechanism, the low output of tungsten light sources at short wavelengths and the loss of contrast sensitivity with decreasing retinal illuminance, it is better to use fairly broad spectrum source of slightly longer wavelength. (After trial and error, it has been found that a 3M color filter part #47 with peak transmittance at 470 nm half band pass ±60 nm worked well.)

3. Shadow Spacing

Periodic grating patterns having a contrast of 40% are easily visible at photopic light levels for spatial frequencies up to 30 cycles/degree. Detailed photographs of latex-filled retinal vessels around the fovea (of Macaque) show capillaries every 28 microns (or 5.7 minutes of arc) or approximately 10 vessels per degree. Periodic grating patterns of 10 cycles/degree can be detected with contrasts of approximately 1% at the fovea but they become invisible at 5 degrees eccentric to the fovea. To the extent grating data can be generalized to the periodic but irregular shadow pattern of the retinal vasculature, the finest detail of the smallest macular capillaries should be easily visible. This is, of course, assuming that image stabilization is appropriately broken.

4. Shadow Movement

Sharpe (12) carefully analyzed the parameters of shadow movement necessary for entoptic perception. He noted: 1) For perception of the fine capillaries, the shadows must move smoothly from one photoreceptor to the next; 2) Since the maximum movement of any shadow is provided by moving the exit pupil of the instrument perpendicular to the orientation of the vessel of interest, perception of the whole vascular bed is best perceived by a random or circular motion of the instruments exit pupil; 3) Despite optimization, the percept of the shadows fade within approximately 60 seconds presumably due to adaptation of pattern detectors.

Previous evidence suggests for longest duration of the entoptic percept the vascular shadows should drift at approximately 150 min of arc/sec and drift over a distance of approximately 40 min of arc. This finding was verified experimentally by changing the diameter of the circular path the exit pupil followed in 1 mm steps and adjusting the velocity of the rotation for each path diameter for optimal vessel perception. This verification process revealed that little, if any, improvement in perception was obtained with an exit pupil rotation diameter greater than 4 mm and an associated rotation frequency of 3.5 Hz. Interestingly, for vessels located 300 microns from the photoreceptor entrance aperture, this stimulus configuration caused each point of the vascular shadow to move in a circle over a distance of approximately 38 min of arc at a velocity of approximately 134 min of arc/sec, a finding consistent with Sharpe's original work (12). However, the distance and velocity over which the vascular shadows move vary with vessel location.

FIG. 9a illustrates the chief ray of the source as it travels its circular path at two different points in time ($t_1$ and $t_2$) 180 degrees apart. Notice that a vessel at a distance s from the entrance aperture of the photoreceptors has a shadow which is displaced by a maximum distance of y when the device's exit pupil is travelling in a circle of diameter T in the entrance pupil of the eye. The geometry of this configuration is more clearly illustrated in FIG. 9b.

Figure 10:
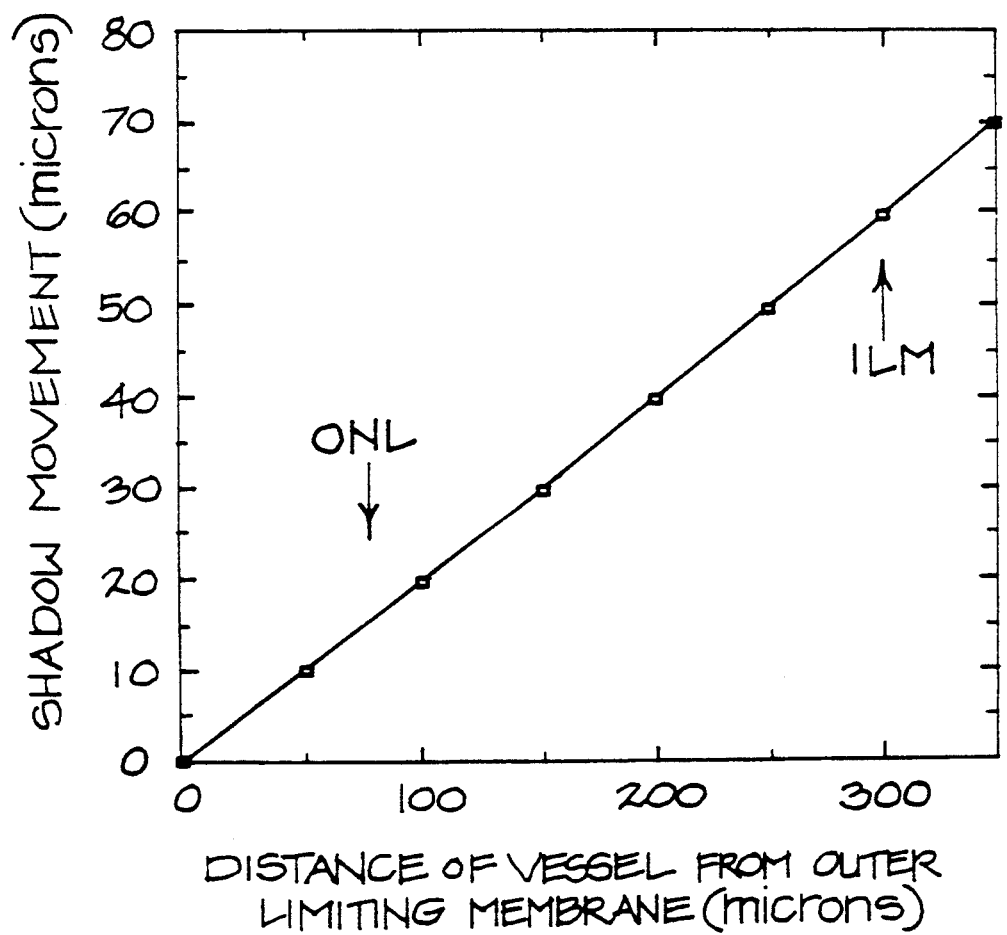

FIG. 10 illustrates the maximum shadow movement perpendicular to the vessel's long axis as a function of the distance of the vessel from the photoreceptors. FIG. 11 displays the variation in shadow velocity perpendicular to the long axis of the capillary as a function of exit pupil location during one complete rotation of the source in the eye's entrance pupil. Calculations for FIGS. 10 and 11 were made using a chief ray moving in a circular 4 mm diameter path in the plane of the eye's entrance pupil. As can be seen in these figures, the shadow of a vessel located in the ONL moves a distance perpendicular to the long axis of the capillary of approximately 59 microns with a velocity varying between 0 and 653 microns/second (0 and 134 min of arc/sec) while a vessel located at the ILM moves approximately 16 microns at a velocity varying between 0 and 171 microns/second (0 an 35 min of arc/sec). More importantly, this stimulus configuration moves any point on the shadow over approximately 35 to 134 photoreceptors per second depending on vessel location. This experimentally determined rotation speed of the source and resulting shadow drift rate is consistent with data from image stabilization experiments that report optimal drift velocities of 15 min of arc/sec for detection of a 10 cycle/degree grating.

The operating principles of the vascular entoptoscope, which provides a view of the retinal vasculature, can be combined with the operating principles of the Blue Field Entoptoscope, (see U.S. Pat. Nos. 4,425,924 and 4,476,878 to Riva et al., incorporated by reference herein for the method and apparatus therein disclosed) which provides a view of the white blood cells. The end product of such a combination will provide a view of the white blood cells moving within the vasculature. This combined unit will, depending on which subunit is turned on, provide a view of: 1) The retinal vasculature by itself; 2) the movement of the white blood cells by itself; or 3) the movement of the white blood cells within the retinal vasculature.

EXAMPLES

The following Examples are presented to describe the best mode of the present invention and are not meant to limit the invention numbers otherwise specified in the claims appended hereto.

Example 1

Precise Mapping Vascular Entoptoscope: The components of the Vascular Entoptoscope are illustrated in FIG. 12.

Source S, a 1 mm pinhole back-illuminated by light from a fiber-optic passing through a blue filter (peak transmittance at 470 nm with a 50 run ½ band pass), rotates at a speed of 3.5 Hz in a circular path 2 mm from, and concentric with, the optical axis of the instrument. Light from S is first collimated by lens $L_1$, and then imaged into the plane of the subject's pupil with unit magnification by lens $L_2$ to form the exit pupil of the device. An iris diaphragm (aperture A) imaged at optical infinity by $L_2$ serves as the field stop for the eye apparatus system.

A second channel provides the subject a view of two dim point sources ($PS_1$ and $PS_2$) optically conjugate with aperture A via beam splitter $B_1$. Point source $PS_1$ is attached to a motorized X-Y positioning plate and serves as a guidelight for marking positions of interest within the field of view. Point source $PS_2$ serves as a stationary fixation point centered on the optical axis of the apparatus. The subject controls the position of $PS_1$ with a joystick, and can thereby locate, with respect to the point of fixation, any point on the retinal vasculature within the field of view that is of interest. A variable voltage signal reflecting the location of moveable point source $PS_1$ is sent from the X-Y position plate to an X-Y plotter for hard-copy documentation of the border of the FAZ. Depending on user preferences and goals, a digital sensor or antilog to digital converter sending its signal to a computer for on-screen display may be the preferred readout device.

Alignment of the subject's pupil to the optical axis of the apparatus and stabilization of the subject's head is obtained with a chin and forehead rest (or bite bar) mobile in three planes (not illustrated in FIG. 12). To insure the subject is properly aligned to the apparatus, a third channel provides a closed-circuit video view of the pupil entry location of the rotating beam and the corneal reflection of the alignment ring AR (a circle of infra-red LED's concentric with the optical axis of the apparatus). The video view of the rotating beam is obtained by deflecting some of the beam from source S at beam splitter $B_2$ onto a front surface mirror (FSM, optically conjugate with the subject's entrance pupil) and back through beam splitter $B_2$ into the video camera (VC). The video view of alignment ring AR is obtained by reflection off the subject's cornea back into the apparatus and reflection at beam splitter $B_2$ into the video camera. By continually observing the information on the monitor, the experimenter can maintain subject/apparatus alignment by adjusting the position of the chin rest.

Example 2

Combined Mapping System

Blue Field Entoptoscope Sub-System: To see the white blood cells entoptically, as opposed to the vessels, all that is necessary is to stop the rotation of the rotating pinhole. The perception of the white blood cells can be enhanced by shifting the wavelength of the source to shorter wavelengths (approximately 435 nm). U.S. Pat. Nos. 4,425,924 and 4,476,878 relate to blood velocity measurements in retinal capillaries utilizing the blue-field entoptic phenomenon. However, given that the complete system is designed to allow the entoptic view of the vessels, the entoptic view of the white blood cells or both the entoptic view of the vessels and the white cells simultaneously, it is best to add a centered (nonrotating) source in the same plane as the source S of FIG. 12. Thus, the centered source is on by itself when viewing the movement of the white blood cells alone and the eccentric rotating source is on by itself when viewing the retinal vasculature alone.

Combined viewing of both the movement of the white blood cells and the retinal vasculature is achieved by having both the rotating source and the centered source on simultaneously and adjusting the intensities of both for optimal perception of both entoptic effects.

While a working model of the instrument that combines both a Blue Field Entoptoscope (which provides a view of the white blood cells as they move through the macular area retinal capillaries) and a Vascular Entoptoscope is not yet available, the results to date show that both systems independently work extremely well. Further, little if any difficulty is anticipated in combining the two units into one and providing the viewer one of three options:

1) An entoptic view of their own retinal vasculature;
2) An entoptic view of the movement of their own white blood cells; and
3) A view of their own white blood cells as they travel through the retinal capillaries.

While each view has its own distinct benefits which are important by themselves, the simultaneous view has several unique advantages which include:

1) Allowing the viewer to determine the rate of blood flow through any capillary of interest;
2) Allowing the viewer to examine vascular irregularities (such as microaneurysms) and how they alter blood flow; and
3) Determining whether or not a particular capillary is patent.

Simpler Devices

Examples of simpler instrument designs which employ the fundamental operating principles of the Vascular Entoptoscope described in Example 1are illustrated in FIGS. 13 through 17. Each example device is designed to optimize the percept of the macular area retinal vasculature by using the fundamental operating principles described in the original submission of a short wavelength (peak wavelength of 340 to 555 nm) source of light which is constrained to enter the eye through a narrow aperture (3 mm or less) moving in space near (or imaged into) the eye in a circular or irregular path (1.5 to 5 mm diameter) at an optimized velocity (between 40 to 60 mm/sec).

Example 3

Simpler Device. Embodiment I

FIG. 13 illustrates schematically a Vascular Entoptoscope which has a small wobbling short wavelength point source (WPS) which is constrained to enter the eye through a narrow aperture by imaging the source near the pupil of the eye using two lenses ($L_1$ and $L_2$). The velocity of movement and path of movement of the narrow aperture is defined by the movement of the wobbling source. The field of view over which vessels can be seen is defined by the field stop (FS) which may or may not include a fixation and/or movable tracing point depending on the desired use. While the clarity of the entoptic percept of the retinal vasculature is essentially independent of refractive error, the clarity of the borders of the field stop and fixation and tracing point, if present, are not. It is not necessarily important that the optical plane of the field stop be seen clearly; however, if clarity of the borders of the field stop and fixation and tracing point is desired, one of two methods can be used: 1) Clarity of the field stop plane can be achieved by changing the location of the field stop with respect to lens 2 ($L_2$) such that user's refractive error is eliminated or minimized; or 2) clarity of the field stop plane can be achieved by positioning the field stop with respect to lens 2 at optical infinity and having the user wear an appropriate distance correction.

FIG. 14 illustrates schematically a device that is in principle identical to the device illustrated in FIG. 13, except that movement of the source image is induced by a wobbling mirror (WM) while the point source (PS) remains stationary.

Example 4

Simpler Device, Embodiment II

FIG. 15 illustrates schematically a second way the fundamental operating principles of the Vascular Entoptoscope can be achieved. Here a uniform short wavelength source (US) back illuminates a field stop (FS) which defines the field of view over which vessels can be seen. As in the apparatus of FIG. 13 the field stop may contain a fixation point and/or a tracing point, if desired. The beam of light entering the eye is constrained to a narrow aperture by a wobbling limiting aperture (WLA) placed near the eye. The velocity of movement and path of movement are defined by the movement of the wobbling aperture as opposed to an image of the source as illustrated schematically in FIGS. 13 and 14. Again, while the clarity of the entoptic percept of the retinal vasculature is essentially independent of refractive error, the clarity of the borders of the field stop is not. As in the instrument designs of FIG. 13 and 14, it is not necessarily important that the borders of the field stop be seen clearly; however, if clarity of the optical plane of the field stop is desired, it can be achieved by either changing the location of the field stop with respect to lens L such that user's refractive error is eliminated or minimized, or it can be achieved by imaging the field stop at optical infinity and having the user wear his/her distance correction.

FIG. 16 illustrates schematically a device that is in principle identical to the device illustrated in FIG. 15 except that no provision is made within the device for seeing the borders of the field stop clearly (i.e., the lens is eliminated). If it is desirable to see the borders of the field stop clearly, an appropriate correcting lens can be placed in front of the eye.

Example 5

Simpler Device, Embodiment III

FIG. 17 illustrates schematically the simplest configuration of the operating principles of the Vascular Entoptoscope. Here the user simply views a uniform short wavelength source (e.g., the sky) through a wobbling limiting aperture placed near the eye. The beam of light entering the eye is constrained to a narrow aperture by a wobbling limiting aperture (WLA) placed near the eye. The velocity of movement and path of movement is defined by the movement of the wobbling aperture. Here there is no variable aperture serving as a field stop limiting the field of view. Instead the field of view is limited by the size and shape of the hole in the wobbling limiting aperture and the size and shape of the eye's pupil.

The following references in pertinent part are incorporated herein for the reasons cited above.

REFERENCES

1. Laatikainen K and Larinkari J: Capillary-free area of the fovea with advancing age. Invest Ophthalmol Vis Sci 16:1154–1157, 1977.
2. Bresnick GH, Condit R, Syrjala S, Palta M, et al: Abnormalities of the foveal avascular zone in diabetic retinopathy. Arch Ophthalmol 102:1286–1293, 1984.
3. Bligard E, de Venecia G, Wallow I, et al: Aging changes of the parafoveolar vasculature: a trypsin digest study. Invest Ophthalmol Vis Sci Suppl 22:8, 1982.
4. Weale RA: Why does the human retina possess a fovea? Nature 212:255–256, 1966.
5. Dartnall HJA and Thomson LC: Retinal oxygen supply and macular pigmentation, Nature 164:876, 1949.
6. Purkinje JE: In Beobachtungen und Versuche zur Physiologie der Sinne. J Calve, Prague, 1819.
7. Bird AC and Weale RA: On the retinal vasculature of the human fovea. Exp Eye Res 19:409–417, 1974.
8. Yeung J, Crock G, Billson F, et al: New observation on retinal microcirculation at the posterior pole in man. Trans Fourth Asia-Pacific Congress Ophthal 25:155–161, 1973.

9. Kluxen G and Wilden E: An entoptic test in diabetic patients. Diabetes Care 10:800–801, 1987.

10. Helmholtz H: Treatise on Physiological Optics, Southall JPC, editor. New York, Dover Publications, Inc., 1962, Vol I pp. 217–218.

11. Shimizu K and Ujiie K: In Structure of ocular vessels. New York, Igaku-Shoin, 1978.

12. Sharpe CR: A Fresh Approach to Stabilized Retinal Images. Part II. J Physiol 217:9–10, 1971.

13. Macular Photocoagulation Study Group: Argon laser photocoagulation for neovascular maculopathy: Three year results from randomized clinical trials. Arch Ophthalmol 104:694–701, 1986.

14. Macular Photocoagulation Study Group: Argon laser photocoagulation for ocular histoplasmosis: Results of a randomized clinical trial. Arch Ophthalmol 101:1347–1357, 1983.

15. Macular Photocoagulation Study Group: Argon laser photocoagulation for idiopathic neovascularization: Results of a randomized clinical trial. Arch Ophthalmol 101:1358–1361, 1983.

16. Macular Photocoagulation Study Group: Krypton laser photocoagulation for neovascular lesions of ocular histoplasmosis: Results of a randomized clinical trial. Arch Ophthalmol 105:1499–1507, 1987.

17. Han DP, Folk JC, and Bratton AR: Visual loss after successful photocoagulation of choroidal neovascularization. Ophthalmol 95:1380–1384, 1988.

The following claims are directed to embodiments of the present invention but it is understood that those skilled in the art may substitute equivalent means and methods to accomplish the desired results.

We claim:

1. An apparatus for entoptically perceiving the macular area retinal vasculature of a human subject's eye under examination, the apparatus comprising:
   (a) a light beam source; and
   (b) a means of continuously directing a light beam from said source into a subject's eye, such that with time the light beam illuminates a same retinal area from constantly varying angles.

2. The apparatus of claim 1 wherein the light beam from said source is variable in intensity and shape.

3. The apparatus of claim 1 wherein the light beam source is a light generator or a light field narrowed through a constraining aperture.

4. An apparatus for entoptically perceiving the macular area retinal vasculature of a human subject's eye under examination, the apparatus comprising:
   (a) a means of directing a light beam into a subject's eye, at angles such that the angle of illumination of said eye's retina by the light beam changes with time; and
   (b) a means to image an aperture of fixed or variable size and shape at optical infinity or other plane of interest as an optical field stop for said apparatus.

5. The apparatus of claim 4 wherein the light beam is of variable intensity and shape.

6. An apparatus for entoptically perceiving the macular area retinal vasculature of a human subject's eye under examination, the apparatus comprising:
   (a) a means of directing a light beam into said eye, at angles such that the angle of illumination of said eye's retina changes with time;
   (b) a means to image an aperture of fixed or variable size and shape at optical infinity or other plane of interest as an optical field stop for said apparatus; and
   (c) a luminous or non-luminous fixation point with a means to image said fixation point on the retina of said eye.

7. The apparatus of claim 6 wherein the field stop is sectionalized to facilitate location of vessels or vessel defects with respect to the fixation point.

8. The apparatus of claim 6 wherein a movable luminous or non-luminous point is contained in the optical field stop.

9. The apparatus of claim 1, 4 or 6 wherein a means is provided to correct for refractive error of said eye.

10. An apparatus for entoptically perceiving the macular area retinal vasculature of a human subject's eye under examination, the apparatus comprising:
    (a) a means of directing a light beam into said eye at angles such that the angle of illumination of said eye's retina by the beam changes with time;
    (b) a means to image an aperture at optical infinity or other plane of interest as an optical field stop for said apparatus, said aperture being of fixed or variable size and shape; and
    (c) a luminous or non-luminous fixation point with a means to image said fixation point on the retina of said eye.

11. The apparatus of claim 10 wherein said light beam is directed in a circular path 2 to 6 mm in diameter.

12. The apparatus of claim 11 wherein said circular path is 3.5 mm in diameter and about centered in said eye's pupil.

13. The apparatus of claim 11 wherein said light beam is directed in an irregular path of greatest dimension about 2 to 6 mm such that all angles of retinal illumination obtainable with a circular path are present.

14. An apparatus for entoptically perceiving the macular area retinal vasculature of a human subject's eye under examination, the apparatus comprising:
    (a) a means of directing said light beam into said eye in a circular path 2 to 6 mm in diameter and about centered in the eye's pupil, said beam being retraced at the rate of about 0.5 to 10 Hz, resulting in an area of retinal illumination in which the angle of illumination of said eye's retina changes with time;
    (b) a means to image an aperture at optical infinity or other plane of interest as an optical field stop for said apparatus, said aperture being of fixed or variable size and shape; and
    (c) a luminous or non-luminous fixation point with a means to image said fixation point on the retina of said eye.

15. The apparatus of claim 14 wherein said light beam is directed in an irregular path of greatest dimension about 2 to 6 mm such that all angles of retinal illumination obtainable with a circular path are present.

16. The apparatus of claim 14 wherein said circular path is retraced at the rate of about 3.5 Hz.

17. The apparatus of claim 14 wherein said aperture is that of an adjustable iris diaphragm.

18. The apparatus of claim 14 wherein said eye's area of retinal illumination comprises a circle and said fixation point is centered within said circle.

19. An apparatus for entoptically perceiving the macular area retinal vasculature of a human subject's eye under examination, the apparatus comprising:
    (a) a means of directing a light beam into said eye in a circular path 2 to 6 mm in diameter and about centered in the eye's pupil, said beam being retraced at the rate of about 0.5 to 10 Hz, and said light having a peak wavelength of about 430 to 555 nm and a half band pass of 0 to 100 nm, resulting in the angle of illumination of said eye's retina changing with time;
(b) a means to image an aperture at optical infinity or other plane of interest as an optical field stop for said apparatus, said aperture being of fixed or variable size and shape; and
(c) a luminous or non-luminous fixation point with a means to image said fixation point on the retina of said eye.

20. The apparatus of claim 19 wherein said light beam is directed in an irregular path of greatest dimension about 2 to 6 mm such that all angles of retinal illumination obtainable with a circular path are present.

21. The apparatus of claim 19 wherein said light beam has a peak wavelength of about 470 nm and a half band pass of ± about 60 nm.

22. An apparatus for entoptically perceiving the macular area retinal vasculature of a human subject's eye under examination, the apparatus comprising:
(a) a means of directing a light beam into said eye through a constraining aperture about 0.1 to 3 mm diameter;
(b) a means of directing a light beam into said eye in a circular path 2 to 6 mm in diameter and about centered in the eye's pupil, said beam being retraced at the rate of about 0.5 to 10 Hz, and said light having a peak wavelength of about 430 to 555 nm and a half band pass of 0 to 100 nm, resulting in an angle of illumination of said eye's retina changing with time;
(c) a means to image an aperture at optical infinity or other plane of interest as an optical field stop for said apparatus, said aperture being of fixed or variable size and shape; and
(d) a luminous or non-luminous fixation point with a means to image said fixation point on the retina of said eye.

23. The apparatus of claim 22 wherein the constraining aperture is an exit pupil.

24. The apparatus of claim 22 wherein said constraining aperture is of irregular shape with greatest dimension about 0.1 to 3 mm.

25. The apparatus of claim 22 wherein said constraining aperture is of irregular shape with greatest dimension about 1 mm.

26. The apparatus of claim 22 wherein said constraining aperture is imaged between said eye's retina and said eye's anterior focal plane.

27. The apparatus of claim 22 wherein said light beam enters said eye through a rotating constraining aperture placed in front of said eye.

28. The apparatus of claim 22 wherein said light beam is diffuse and of uniform intensity.

29. An apparatus for entoptically perceiving and mapping the macular area retinal vasculature of a human subject's eye under examination, the apparatus comprising:
(a) a means to establish and maintain translational and rotational alignment of said eye with said apparatus;
(b) a light source of variable intensity illuminating an aperture which is imaged in or near the eye's entrance pupil plane to form an exit pupil of the apparatus and a means of moving said exit pupil along a path in space;
(c) a means of imaging said exit pupil into said eye's entrance pupil at angles such that the angle of illumination of an illuminated area of said eye's retina changes with time;
(d) a means to image an aperture stop at optical infinity or other plane of interest to correct for any refractive error as an optical field stop for said apparatus, said aperture being of variable size and shape;
(e) a luminous or nonluminous fixation point and a means to image said fixation point on the retina of said eye;
(f) a luminous or nonluminous tracking point and a means to form an image of the tracking point on the retina of the eye;
(g) a means of moving said tracking point retinal image with respect to said fixation point retinal image;
(h) a means of transducing movement of said tracking point retinal image to yield coordinates of its location on said eye's retina with respect to said fixation point retinal image;
(i) a means of compiling or displaying coordinates of said tracking point retinal image movement, said compilation or display comprising a map of tracking point retinal image positions with respect to said fixation point retinal image; and
(j) a means to detect and indicate magnitude and direction of translation of said eye with respect to said apparatus.

30. The apparatus of claim 29 wherein the aperture in step (b) is an entrance pupil of the apparatus.

31. The apparatus of claim 29 wherein the tracking point is a light source.

32. The apparatus of claim 29 wherein the means to establish and maintain rotational alignment is a bite bar for the subject to orally embrace or a chin and forehead rest.

33. The apparatus of claim 29 wherein path of movement of the apparatus exit pupil is circular, about 2 to 6 mm in diameter and about centered in the eye's pupil.

34. The apparatus of claim 29 wherein the path of movement of the apparatus exit pupil is circular, 4 mm in diameter and about centered in the eye's pupil.

35. The apparatus of claim 29 wherein the path of movement of the apparatus exit pupil is circular, being retraced at the rate of about 0.5 to 10 Hz.

36. The apparatus of claim 29 wherein the path of movement of the apparatus exit pupil is circular, being retraced at the rate of about 3.5 Hz.

37. The apparatus of claim 29 wherein said aperture stop is that of an adjustable iris diaphragm.

38. The apparatus of claim 29 wherein the area of retinal illumination is a circle and said fixation point retinal image is within said circle.

39. The apparatus of claim 29 wherein the area of retinal illumination is a circle and said fixation point retinal image is centered within said circle.

40. The apparatus of claim 29 wherein said light source has a peak wavelength of about 430 to 555 nm and a half band pass of 0 to 100 nm.

41. The apparatus of claim 29 wherein said light source has a peak wavelength of about 470 nm and a half band pass of about ±60 nm.

42. The apparatus of claim 29 wherein the exit pupil of the apparatus is circular with a diameter of about 0.1 to 3 mm.

43. The apparatus of claim 29 wherein the exit pupil of the apparatus is circular with a diameter of about 1.0 or less.

44. The apparatus of claim 29 wherein the exit pupil of the apparatus is imaged in or near said eye's entrance pupil plane.

45. The apparatus of claim 29 wherein the exit pupil of the apparatus is imaged between said eye's anterior focal plane and the said eye's retina.

46. The apparatus of claim 29 wherein said light source is diffuse and of uniform intensity.

47. The apparatus of claim 29 where said indication of magnitude and direction of translation of said eye with respect to said apparatus in step (j) is visible.

48. The apparatus of claim 29, where said indication of magnitude and direction of translation of said eye with respect to said apparatus in step (j) is sensed by an external operator.

49. The apparatus of claim 29 where said indication of magnitude and direction of translation of said eye with respect to said apparatus in step (j) is detected by a sensor and monitored by a computer.

50. The apparatus of claim 29 wherein tracking point retinal image coordinates of step (h) are corrected manually for retinal image translation caused by any translation of said eye with respect to said apparatus.

51. The apparatus of claim 29 wherein tracking point retinal image coordinates of step (h) are corrected by automatic computation for retinal image translation caused by translation of said eye with respect to said apparatus.

52. The apparatus of claim 29 wherein tracking point retinal image coordinates in step (i) are calibrated in units of length measured on said retinal surface.

53. The apparatus of claim 29 wherein tracking point retinal image coordinates in step (i) are calibrated in units of angular subtense.

54. The apparatus of claim 29 wherein said means of moving said tracking point retinal image of step (h) is a joystick or similar x-y controller.

55. An apparatus for entoptically perceiving and mapping white blood cell circulation and macular retinal vasculature of a human subject's eye under examination, the apparatus comprising:
(a) a means to establish and maintain translational alignment of a subject's eye with the apparatus;
(b) a light source of variable intensity illuminating an aperture which is imaged in or near the eye's entrance pupil plane to form an exit pupil of the apparatus, and a means of moving said exit pupil along a path in space;
(c) a means of imaging said device apparatus exit pupil into said eye's entrance pupil at angles such that the angle of retinal illumination of said eye's retina changes with time;
(d) a means to image an aperture stop at optical infinity or other plane of interest to correct for refractive error as an optical field stop for said apparatus, said aperture being of variable size and shape;
(e) a luminous or nonluminous fixation point and a means to image said fixation point on the retina of said eye;
(f) a luminous or nonluminous tracking point and a means to form an image of the tracking point on the retina of the eye;
(g) a means of moving said tracking point retinal image with respect to said fixation point retinal image;
(h) a means of transducing movement of said tracking point retinal image to yield coordinates of its location on said eye's retina with respect to said fixation point retinal image;
(i) a means of compiling or displaying said coordinates of said tracking point retinal image movement, said compilation or display comprising a map of said tracking point retinal image positions with respect to said fixation point retinal image;
(j) a means to detect and indicate magnitude and direction of translation of said eye with respect to said apparatus;
(k) a blue-field light source of variable intensity and a means to illuminate said eye's retina with said blue-field light source;
(l) a luminous or nonluminous speed-comparator and a means to form a retinal image of said speed-comparator on said eye's retina, said speed-comparator retinal image being of a size about equal to said entoptically perceived white blood cells;
(m) a means of causing said speed-comparator retinal image to move along a fixed or variable path on said eye's retina at a fixed or variable velocity; and
(n) a means of rotating and translating said speed comparator retinal image on said eye's retina.

56. The apparatus of claim 55 wherein the exit pupil of the apparatus has a circular path of movement about 2 to 6 mm in diameter and about centered in the eye's pupil.

57. The apparatus of claim 55 wherein the exit pupil of the apparatus has a circular path of movement 4 mm in diameter and about centered in the eye's pupil.

58. The apparatus of claim 55 wherein the exit pupil of the apparatus has a circular path of movement which is retraced at the rate of about 0.5 to 10 Hz.

59. The apparatus of claim 55 wherein the exit pupil of the apparatus has a circular path of movement which is retraced at the rate of about 3.5 Hz.

60. The apparatus of claim 55 wherein said aperture stop is that of an adjustable iris diaphragm.

61. The apparatus of claim 55 wherein said eye's area of retinal illumination is a circle and said fixation point retinal image is within said circle.

62. The apparatus of claim 55 wherein said eye's area of retinal illumination comprises a circle and said fixation point retinal image is centered within said circle.

63. The apparatus of claim 55 wherein said light source has a peak wavelength of about 430 nm and 555 nm and a half band pass of 0 to 100 nm.

64. The apparatus of claim 55 wherein said light source has a peak wavelength of about 470 nm and a half band pass of about ±60 nm.

65. The apparatus of claim 55 wherein the exit pupil of the apparatus is circular with a diameter of about 0.1 to 3 mm.

66. The apparatus of claim 55 wherein the exit pupil of the apparatus is circular with a diameter of about 1.0 mm or less.

67. The apparatus of claim 55 wherein the exit pupil of the apparatus is imaged in or near said eye's entrance pupil plane.

68. The apparatus of claim 55 wherein the exit pupil of the apparatus is imaged between said eye's anterior focal plane and said eye's retina.

69. The apparatus of claim 55 wherein said light source is diffuse and of uniform intensity.

70. The apparatus of claim 55 where said indication of magnitude and direction of translation of said eye with respect to said apparatus in step (j) is visible.

71. The apparatus of claim 55 where said indication of magnitude and direction of translation of said eye with respect to said apparatus in step (j) is sensed by an external operator.

72. The apparatus of claim 55 where said indication of magnitude and direction of translation of said eye with respect to said apparatus in step (j) is detected by a sensor and monitored by a computer.

73. The apparatus of claim 55 wherein said tracking point retinal image coordinates of step (h) are corrected manually for retinal image translation caused by translation of said eye with respect to said apparatus.

74. The apparatus of claim 55 wherein said tracking point retinal image coordinates of step (h) are corrected by automatic computation for retinal image translation caused by translation of said eye with respect to said apparatus.

75. The apparatus of claim 55 wherein said tracking point retinal image coordinates in step (i) are calibrated in units of length measured on said retinal surface.

76. The apparatus of claim 55 wherein said tracking point retinal image coordinates in step (i) are calibrated in units of angular subtense.

77. The apparatus of claim 55 wherein said means of moving said tracking point retinal image of step (h) is a joystick or similar x-y controller.

78. The apparatus of claim 55 wherein said blue-field light source has a dominant wavelength of about 430 to 500 nm.

79. The apparatus of claim 55 wherein light from said blue-field light source is directed coaxially with the instrument's optical axis.

80. The apparatus of claim 55 wherein said blue-field light source is about 50% of total light.

81. The apparatus of claim 55 wherein said blue-field light is applied to said retina constantly or intermittently in alternation with the light source of step (a) at a rate which minimizes perceptual flicker and having a duty cycle variable to optimize perception of both retinal vessels and white blood cells.

82. The apparatus of claim 55 wherein said retinal path of said speed-comparator light image is curved to mimic the course of a retinal vessel.

83. The apparatus of claim 55 wherein said retinal path of said speed-comparator light image is straight.

84. The apparatus of claim 55 wherein said retinal path of said speed-comparator retinal image is about $10^{-4}$ to $10^{-3}$ m in length.

85. The apparatus of claim 55 wherein said velocity of the speed comparator can be adjusted to mimic velocity of a white corpuscle passing through vasculature.

* * * * *